(12) United States Patent
Hudson et al.

(10) Patent No.: US 9,289,417 B2
(45) Date of Patent: Mar. 22, 2016

(54) COMPOUNDS AND METHODS FOR THE MODULATION OF SULFILIMINE BOND FORMATION

(75) Inventors: Billy G. Hudson, Brentwood, TN (US); Roberto Vanacore, Nashville, TN (US); Gautam Bhave, Nashville, TN (US); Vadim Pedchenko, Nolensville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 13/376,687

(22) PCT Filed: Jun. 11, 2010

(86) PCT No.: PCT/US2010/038341
§ 371 (c)(1),
(2), (4) Date: Mar. 28, 2012

(87) PCT Pub. No.: WO2010/144822
PCT Pub. Date: Dec. 16, 2010

(65) Prior Publication Data
US 2012/0177656 A1 Jul. 12, 2012

Related U.S. Application Data

(60) Provisional application No. 61/186,265, filed on Jun. 11, 2009.

(51) Int. Cl.
*A61K 31/4164* (2006.01)
*A61K 31/05* (2006.01)
*A61K 45/06* (2006.01)

(52) U.S. Cl.
CPC ............. *A61K 31/4164* (2013.01); *A61K 31/05* (2013.01); *A61K 45/06* (2013.01)

(58) Field of Classification Search
CPC .................................................. A61K 31/4614
See application file for complete search history.

(56) References Cited

U.S. PATENT DOCUMENTS 3,558,778 A * 1/1971 Klingbail ....................... 514/184
6,365,616 B1 * 4/2002 Kohn et al. .................... 514/396

OTHER PUBLICATIONS

Aceves C, Anguiano B, Delgado G. Is iodine a gatekeeper of the integrity of the mammary gland? J Mammary Gland Biol Neoplasia. Apr. 2005;10(2):189-96.*
Bhave G, Cummings CF, Vanacore RM, Kumagai-Cresse C, Ero-Tolliver IA, Rafi M, Kang JS, Pedchenko V, Fessler LI, Fessler JH, Hudson BG. Peroxidasin forms sulfilimine chemical bonds using hypohalous acids in tissue genesis. Nat Chem Biol. Sep. 2012;8(9):784-90.*
Weiss SJ Peroxidasin: tying the collagen-sulfilimine knot. Nat Chem Biol. Sep. 2012;8(9):740-1.*
"*Homo sapiens* peroxidasin homolog (*Drosophila*) (PXDN), mRNA," NCBI Reference Sequence: NM_012293.1, 1994.
"Peroxidasin homolog precursor [*Homo sapiens*]" NCBI Reference Sequence: NP_036425.1, 1999.
Borza et al., "Goodpasture autoantibodies unmask cryptic epitopes by selectively dissociating autoantigen complexes lacking structural reinforcement: novel mechanisms for immune privilege and autoimmune pathogenesis," *J. Biol. Chem.*, 280(29):27147-27154, 2005.
Elgawish et al., "Involvement of hydrogen peroxide in collagen cross-linking by high glucose in vitro and in vivo," *J. Biol. Chem.*, 271(22): 12964-12971, 1996.
Hudson et al., "Alport's syndrome, Goodpasture's syndrome, and type IV collagen," *N. Engl. J. Med.*, 348:2543, 2003.
Larios et al., "Oxidative protein cross-linking reactions involving L-tyrosine in transforming growth factor-β1-stimulated fibroblasts," *J. Biol. Chem.*, 276(20): 17437-17441, 2001.
PCT International Preliminary Report on Patentability issued in PCT/US2010/038341, mailed Dec. 22, 2011.
PCT International Search Report and Written Opinion issued in PCT/US2010/038341, dated Nov. 8, 2010.
Péterfi et al., "Peroxidasin is secreted and incorporated into the extracellular matrix of myofibroblasts and fibrotic kidney," *Am J Pathol.*, 175(2): 725-735, 2009.
Siebold et al., "The arrangement of intra- and intermolecular disulfide bonds in the carboxyterminal, non-collagenous aggregation and cross-linking domain of basement-membrane type IV collagen," *Eur. J. Biochem.*, 176(3):617-624, 1988.
Sundaramoorthy et al., "Crystal structure of NC1 domains. Structural basis for type IV collagen assembly in basement membranes," *J. Biol. Chem.*, 277:31142, 2002.
Than et al., "The 1.9-A crystal structure of the noncollagenous (NC1) domain of human placenta collagen IV shows stabilization via a novel type of covalent Met-Lys cross-link," *Proc Natl Acad Sci USA*, 99(10):6607-6612, 2002.
Than et al., "The NC1 dimer of human placental basement membrane collagen IV: does a covalent crosslink exist?" *Biological Chemistry*, 386:759, 2005.
Vanacore et al., "A role for collagen IV cross-links in conferring, immune privilege to the Goodpasture autoantigen: structural basis for the crypticity of B cell epitopes,"*J Biol Chem.*, 283(33):22737-22748, 2008.
Vanacore et al., "A sulfilimine bond identified in collagen IV," *Science*, 325(5945): 1230-1234, 2009.
Vanacore et al., "Identification of S-hydroxylysyl-methionine as the covalent cross-link of the noncollagenous (NC1) hexamer of the alpha1alpha1alpha2 collagen IV network: a role for the post-translational modification of lysine 211 to hydroxylysine 211 in hexamer assembly," *J Biol Chem.*, 280(32): 29300-29310, 2005.
Vanacore et al., "The α1.α2 network of collagen IV. Reinforced stabilization of the noncollagenous domain-1 by noncovalent forces and the absence of Met-Lys cross-links," *J. Biol. Chem.*, 279(43): 44723-44730, 2004.

* cited by examiner

*Primary Examiner* — Paul Zarek
(74) *Attorney, Agent, or Firm* — Parker Highlander PLLC

(57) ABSTRACT

Methods for regulating the formation of a sulfilimine crosslink in a subject by administering a sulfilimine crosslink modulator are disclosed The sulfilimine modulator may inhibit or create a sulfilimine crosslink and maybe useful for treating a disease, such as cancer The sulfilimine crosslink may be between two or more peptides.

6 Claims, 17 Drawing Sheets

FIG. 4

```
                           93                                                           211
Hsa_A1         YWLSTPEPMPMSMAPITGENIRPFISRC------------RPTPSTLKAGE--LRTHVSRC    NP_001836.2
Hsa_A2         YWLSTTAPLP--MMPVAEDEIKPYISRC------------SPSADTLKAGL--IRTHISRC    NM_001846.2
Hsa_A3         YWLSTPALMPMNMAPITGRALEPYISRC------------KPIPSTVKAGE--LEKIISRC    ABX71213.1
Hsa_A4         YWLASAAPLP--MMPLSEEAIRPYVSRC------------APAPDTLK[E]SQA-QRQKISRC  X81053.1
Hsa_A5         YWLSTPEPMPMSMQPLKGQSIQPFISRC------------KPQSETLKAGD--LRTRISRC    ABW24668.1
Hsa_A6         YWLSTTAPIP--MMPVSQTQIPQYISRC------------LPVSETLKAGQ--LGTRVSRC    AL136080.6

Cintestinalis_A1  FWLSTPEPFPMSMEAVTGSAIEPYISRC------------QPISETLKAGT--LRQRVSRC   XP_2120982.1
Cintestinalis_    YWLSTTAAIP--MMPVSVDMVPEYISRC------------TPEMETLKAGN--LRTRVSRC   XP_2119477.1
Spu_A2            YWLTTNEPLP--MMPLMNQQIDPYISRC------------IPRKRTIKSGQ--LQSVVSRC   NP_999676.1
Spu_A3            YWLSTEEPMPMNMAPIRGGQLQPFISRC------------MPQSETLKAGS--LRTRVSRC   NP_999631.1
Dme_A1            FWLTTNAAIP--MMPVENIEIRQYISRC------------RPQQQTIKAGE--RQSHVSRC   AAA28404.1
Dme_A2            LWLSTAEPMPMTMTPIQGRDLMKYISRC------------QPRQQTLKADF--TSKISRC    AAB64082.1
Cel_A1            FWLSTDEPMTPMMNPVTGTAIRPYISRC------------KPMSQTLKAGG--LKDRVSRC   AAB59179.1
Cel_A2            YWLSTSEAIP--MMPVNEREIEPYISRC------------VPESQTLKSGN--LRTRVSRC   AAA27989.1
Bmalayi           FWLSTAEPMTQMMNPVSGTAIRPYISRC------------KPMSQTLKAGG--LKDRVSRC   XP_1902932.1
Asc_suum_A2       YWLSTTAPIP--MMPVSEGGIEPYISRC------------IPESETLKAGS--LRTRVSRC   AAA18014.1
Nvectensis_A2     FWLSTPEPIP--MMPVQETNVQPYIGRC------------IPRPETLKAGN--LRERVSRC   XP_162265.1

Hydra_mag_A1      FWLSTAEKPK--[E]APSSGADLENYISRC----------VPKSEIILER-N--LKARVSRC  XP_2157001.1
Hydra_vul_A1      FWLSTAEKPK--[E]APSSGADLENYISRC----------VPKFEILER-N--LKARVSRC   AAG40720.1
Sjapanicum        YWLATLVPRS--[E]QIPVNQTADQIARC-----------KPVGFVMKAAEGPVLNNVSKC   AAX25734.2
Pjarrei_A4        YWLSTNATRPPIP-VSGSDIEEHISRC-------------DTEPGTY[P]VSD-IEKRLSRC  CAA65083.1
Tadhaerens_A1     YWLSASLAPS--[Y]VPISGSNIAPYIGRC----------PPTQQVL[S]ASAT-S-SEISRC EDV21329.1
Tadhaerens_A2     YWLSTSLTPA--[M]MTLTGLNIRPYISRC----------PPTATVL[N]FNDN-PQSYISRC EDV21231.1
                  *.**        :  :.**                    .                 ***
                                                         XKA
                                                          S
                                                          G
```

COMPOUNDS AND METHODS FOR THE MODULATION OF SULFILIMINE BOND FORMATION

This application is a national phase application under 35 U.S.C. §371 of International Patent Application No. PCT/US2010/038341 filed Jun. 11, 2010 which claims benefit of priority to U.S. Provisional Application Ser. No. 61/186,265, filed Jun. 11, 2009, the entire contents of both applications being hereby incorporated by reference.

This invention was made with government support under grant numbers DK065123 and DK18381 awarded by the National Institutes of Diabetes and Digestive and Kidney Diseases of the National Institutes of Health. The government has certain rights in the invention.

BACKGROUND OF THE INVENTION

1. Field of the Invention

The present invention relates generally to the fields of biology and medicine. In particular, the invention relates to the modulation of the sulfilimine bond between peptides and treatment of conditions by the modulation of the same.

2. Description of Related Art

Collagen IV networks are ancient proteins of basement membranes, a specialized form of extracellular matrix, that underlie epithelia in metazoa from sponge to human. Collagen IV molecules are assembled into networks that serve as a scaffold for the assemblage of BM components (Hudson et al., 2003). The networks confer structural integrity to tissues, serve as scaffolds for the assembly of other macromolecular components, and serve as ligands for integrin cell-surface receptors that mediate cell adhesion, migration, growth and differentiation (Moser et al., 2009; Hynes, 2002; Yurchenco and Furthmayr, 1984). The networks participate in signaling events in *Drosophila* development, in the clustering of receptors in the development of mammalian neuromuscular junction (Fox et al., 2007), and they are involved in autoimmune and genetic diseases (Gould et al., 2006; Gould et al., 2005; Hudson et al., 2003). The networks are assembled by oligomerization of triple-helical protomers by end-to-end associations and by intertwining of triple helices through their N- and C-terminal domains (Khoshnoodi et al., 2008; Khoshnoodi et al., 2006). At the C-terminus, two protomers associate through their trimeric non-collagenous (NC1) domains forming a hexamer structure. The protomer-protomer interface is covalently crosslinked, a key reinforcement that strengthens the structural integrity of networks. In the case of humans, the crosslink also confers immune privilege to the collagen IV antigen of Goodpasture autoimmune disease (Vanacore et al., 2008; Borza et al., 2005).

The quest for the chemical nature of these crosslinks has been the subject of numerous investigations over the last two decades; yet, the identity of the covalent bond remained unknown. Initially, the crosslinks were identified as disulfide bonds (Siebold et al., 1988), which were subsequently ruled out by the x-ray crystal structure of NC1 hexamers (Sundaramoorthy et al., 2002; Than et al., 2002). Electron density maps suggested connectivity between Methionine-93 ($Met^{93}$) and Lysine-211 (Lys211) at the interface of adjoining protomers (Than et al., 2002); however, the connectivity is gradually degraded by x-rays, rendering precise characterization a challenge for structural analysis by crystallography (Than et al., 2005; Vanacore et al., 2004).

SUMMARY OF THE INVENTION

Thus, in accordance with the present invention, there is provided a method of treating a disease in an subject, comprising administering to the subject an effective amount of a sulfilimine crosslink inhibitor. The sulfilimine crosslink inhibitor may inhibit the formation of a sulfilimine crosslink between two or more peptides, for example, where at least one of the peptides is collagen IV. The sulfilimine crosslink inhibitor may be a selective or a non-selective inhibitor. The non-selective inhibitor may be a peroxidase inhibitor, such as methimazole or phloroglucinol. The sulfilimine crosslink inhibitor may be a nucleic acid, a protein, a peptide, an antibody, or a small molecule. The antibody may be a monoclonal antibody that binds immunologically to human peroxidasin, the peptide may be a fragment of human peroxidasin or a human peroxidasin substrate, or the nucleic acid may be an siRNA or miRNA that inhibits synthesis of human peroxidasin.

The subject may be a human. The inhibitor may be administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctivally, intravesicularly, mucosally, intrapericardially, intraumbilically, orally, by inhalation, by injection, by infusion, by continuous infusion, by localized perfusion bathing target cells directly, via a catheter, or via a lavage. The disease may be is a helmith infection, such as ascariasis, dracunculiasis, elephantiasis, hookworm, lymphatic filariasis, onchocerciasis, schistosomiasis, or trichuriasis. The disease may be cancer, such as breast cancer, lung cancer, prostate cancer, ovarian cancer, brain cancer, liver cancer, cervical cancer, colorectal cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. The sulfilimine crosslink inhibitor may be administered to a cancer patient locally to the tumor, by direct intratumoral injection, by injection into tumor vasculature, or systemically.

The method may further comprise identifying a subject in need of treatment. Such subject may have a family or patient history of cancer, or have symptoms of cancer. The method may also further comprise a treatment selected from the group consisting of administering a pharmaceutically effective amount of a second drug, radiotherapy, gene therapy, and surgery. The sulfilimine crosslink inhibitor may inhibit angiogenesis or may inhibit tumor growth. The In another embodiment, there is provided a method of modulating the formation of a sulfilimine crosslink in a subject, comprising administering to the subject an effective amount of a sulfilimine crosslink modulator. The sulfilimine crosslink inhibitor may inhibit the formation of a sulfilimine crosslink between two or more peptides, for example, where at least one of the peptides is collagen IV. The sulfilimine crosslink inhibitor may be a selective or a non-selective inhibitor. The non-selective inhibitor may be a peroxidase inihbitor, such as methimazole or phloroglucinol. The sulfilimine crosslink inhibitor may be a nucleic acid, a protein, a peptide, an antibody, or a small molecule. The antibody may be a monoclonal antibody that binds immunologically to human peroxidasin, the peptide may be a fragment of human peroxidasin or a human peroxidasin substrate, or the nucleic acid may be an siRNA or miRNA that inhibits synthesis of human peroxidasin.

In still another embodiment, there is provided a method of inhibiting the formation of a sulfilimine crosslink in a subject, comprising administering to the subject an effective amount of a sulfilimine crosslink inhibitor. The sulfilimine crosslink inhibitor may inhibit the formation of a sulfilimine crosslink between two or more peptides, for example, where at least one of the peptides is collagen IV. The sulfilimine crosslink inhibitor may be a selective or a non-selective inhibitor. The non-selective inhibitor may be a peroxidase inihbitor, such as methimazole or phloroglucinol. The sulfilimine crosslink inhibitor may be a nucleic acid, a protein, a peptide, an antibody, or a small molecule. The antibody may be a monoclonal antibody that binds immunologically to human peroxidasin, the peptide may be a fragment of human peroxidasin or a human peroxidasin substrate, or the nucleic acid may be an siRNA or miRNA that inhibits synthesis of human peroxidasin.

In still a further embodiment, there is provided a method of creating or strengthening a sulfilimine crosslink, comprising administering to the subject an effective amount of a sulfilimine crosslink modulator. For example, where a sulfilimine crosslink is created, the crosslink may be created within a peptide or a biomolecule, or between two or more peptides or a biomolecule. The sulfilimine crosslink may be created chemically or enzymatically. Where sulfilimine crosslink is strengthened, the crosslink may be strengthened within a peptide or a biomolecule, or between two or more peptides. The sulfilimine crosslink may be strengthened chemically or enzymatically. The method may further comprise creating a supramolecular complex.

It is contemplated that any embodiment discussed in this specification can be implemented with respect to any method or composition of the invention, and vice versa. Furthermore, compositions of the invention can be used to achieve methods of the invention.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be better understood by reference to one or more of these drawings in combination with the detailed description of specific embodiments presented herein.

(FIG. 1A) A composite of the multiple-charged (+4, +5, and +6) ions of the crosslinked tryptic peptide complex observed in a full-scan MS spectrum. The arrow indicates the monoisotopic peak in the isotopic envelope of each ion. The final observed mass for the crosslinked Tp-peptide complex was obtained by averaging the peptide mass values obtained by deconvolution of each charge-state ion. (FIG. 1B) $MS^2$ spectrum showing the fragmentation by collision-induced dissociation of the m/z 1003.1014 (+5) ion. The bottom panel shows the isotopic envelope for each ion and the mass difference of each fragment with respect to the uncrosslinked peptides (SEQ ID NOS: 2 and 3). (FIG. 1C) NMR studies showing the overlay of $^1H$-$^1H$ correlated spectroscopy COSY (black) and standard HMQC (blue) spectra in 50 mM phosphate buffer, pH=7.0, 20° C. (FIG. 1D) Edited $^1H$-$^{13}C$ HSQC spectrum of an expanded portion of panel C in which the methyl groups of Val, Leu, Thr, Iso, and Met are expected. Correlation peaks are color-coded according to multiplicity edited HSQC spectra, optimized for correlation selection of $CH_2$ (red), $CH/CH_3$ (blue) and CH (green) only. Several peaks contain overlapping signals from $CH_3$ and CH groups are indicated by the blue/green striped coloring.

(FIG. 2A) The uncrosslinked tryptic peptides (SEQ ID NOS: 2 and 3), T-3599.689 and T-1412.799, derived from the α1-NC1 domain, display the side chains of $Met^{93}$ and $Hyl^{211}$, respectively. T-5012.488 corresponds to the total theoretical mass of both peptides. The sulfilimine double bond crosslinking the tryptic peptides is shown. The difference between the theoretical (theo) and observed (obs) mass reveals that two hydrogen atoms are lost upon sHM crosslink formation. Fragmentation of the sulfilimine bond by CID produces peptide fragments containing modified side chains for $Met^{93}$ and $Hyl^{211}$ as indicated. However, chemical reduction of the crosslinked Tp-peptides peptides with DTT cleaves the sulfilimine linkage and recovers $Met^{93}$ and $Hyl^{211}$, as indicated vide infra (FIG. 2B) Crosslinked Tp-peptides were separated by gel filtration chromatography before (green) and after incubation in 100 mM DTT at room temperature (red) and 80° C. (blue). The arrows indicate the identity of each chromatographic peak as revealed by MS analysis.

FIG. 4. Multiple sequence alignment of collagen IV NC1 domain sequences encompassing $Met^{93}$ and $Lys^{211}$. Lys211 and $Met^{93}$ are shown in bold. Reference numbers for each sequence are shown on the right (SEQ ID NOS: 4 through 26). Conserved amino acid residues are indicated with an asterisk (*). Semi-conserved residues are indicated with a colon (:). The hydroxylation motif for lysyl hydroxylase, X-K-(A/S/G) is shown at the bottom of the alignment. Abbreviations are as follow: Homo sapiens (Hsa), Ciona Intestinalis (Cintestinalis), Streptosporangium purpuratum (Spu), Drosophila melanogaster (Dme), *Caenorhabditis elegans* (Cel), *Brugia malayi* (Bmalayi), *Ascaris Suum* (Asc_suum), *Nematostella vectensis* (Nvectensis), *Hydra magnipapillata* (Hydra_mag), *Hydra vulgaris* (Hydra_vul), *Schistosoma japonicum* (Sjaponcum), *Trichoplax adhaerens* (Tadhaerens). The alignments were generated with ClustalW.

(FIG. 5A) The y- and b-ion series not only confirm the sequences of T-1412.799 peptide, but also that the location of the mass change of +45.984 mass units corresponds to the side chain of Hyl$^{211}$ (SEQ ID NO: 2). (FIG. 5B) FTICR-MS$^3$ fragmentation profile for the m/z 1184.900 ion which verified the peptide sequence (SEQ ID NO: 3); it was not possible to determine which methionine residue (M91 or M$^{93}$) lost the 48.013 mass units. The b- and y-ion series are shown in blue and red color, respectively.

(FIG. 6A) [insert] (FIG. 6B) FTICR-MS spectrum for the PPE-complex in which a doubly (m/z 762.8824) and triply (m/z 508.5898) charged ions are observed. The average of ten scans gives an observed mass of 1522.746±0.001 as shown in the table. This mass value is 2.018±0.001 mass units smaller than theoretical monoisotopic mass of the PPE-complex (1524.764). (FIG. 6C) FTICR-MS/MS fragmentation of the doubly-charged ion (m/z 762.8824) which generated two fragment ions (red). In addition, many ions derived from the Hyl$^{211}$-containing fragment can also be observed (blue) (SEQ ID NO: 28). (FIG. 6D) MS$^3$ spectrum for the singly-charged m/z 488.216 ion corresponding to the Met$^{93}$-containing peptide which lost 48 mass units from the Met$^{93}$ side chain. (FIG. 6E) MS$^3$ spectrum for the doubly-charged m/z 518.775 ion corresponding to the Hyl$^{211}$-containing peptide which carries 46 mass units covalently attached to Hyl$^{211}$. The b- and y-ion series are shown in blue and red color, respectively.

DETAILED DESCRIPTION OF ILLUSTRATIVE EMBODIMENTS

Collagen IV networks are ancient proteins of basement membranes (BM), a specialized form of extracellular matrix, that underlie epithelia in metazoa from sponge to human. Collagen IV molecules are assembled into networks that serve as a scaffold for the assemblage of BM components (Hudson et al., 2003). The networks confer structural integrity to tissues, serve as scaffolds for the assembly of other macromolecular components, and serve as ligands for integrin cell-surface receptors that mediate cell adhesion, migration, growth and differentiation (Moser et al., 2009; Hynes, 2002; Yurchenco and Furthmayr, 1984). The networks also participate in signaling events in *Drosophila* development, in the clustering of receptors in the development of mammalian neuromuscular junction (Fox et al., 2007), and they are involved in autoimmune and genetic diseases (Gould et al., 2006; Gould et al., 2005; Hudson et al., 2003).

The Collagen IV networks are assembled by oligomerization of triple-helical protomers by end-to-end associations and by intertwining of triple helices through their N- and C-terminal domains (Khoshnoodi et al., 2008; Khoshnoodi et al., 2006). At the C-terminus, two protomers associate through their trimeric non-collagenous (NC1) domains forming a hexamer structure. The protomer-protomer interface is covalently crosslinked, a key reinforcement that strengthens the structural integrity of networks. In the case of humans, the crosslink also confers immune privilege to the collagen IV antigen of Goodpasture autoimmune disease (Vanacore et al., 2008; Borza et al., 2005).

Figure 3:
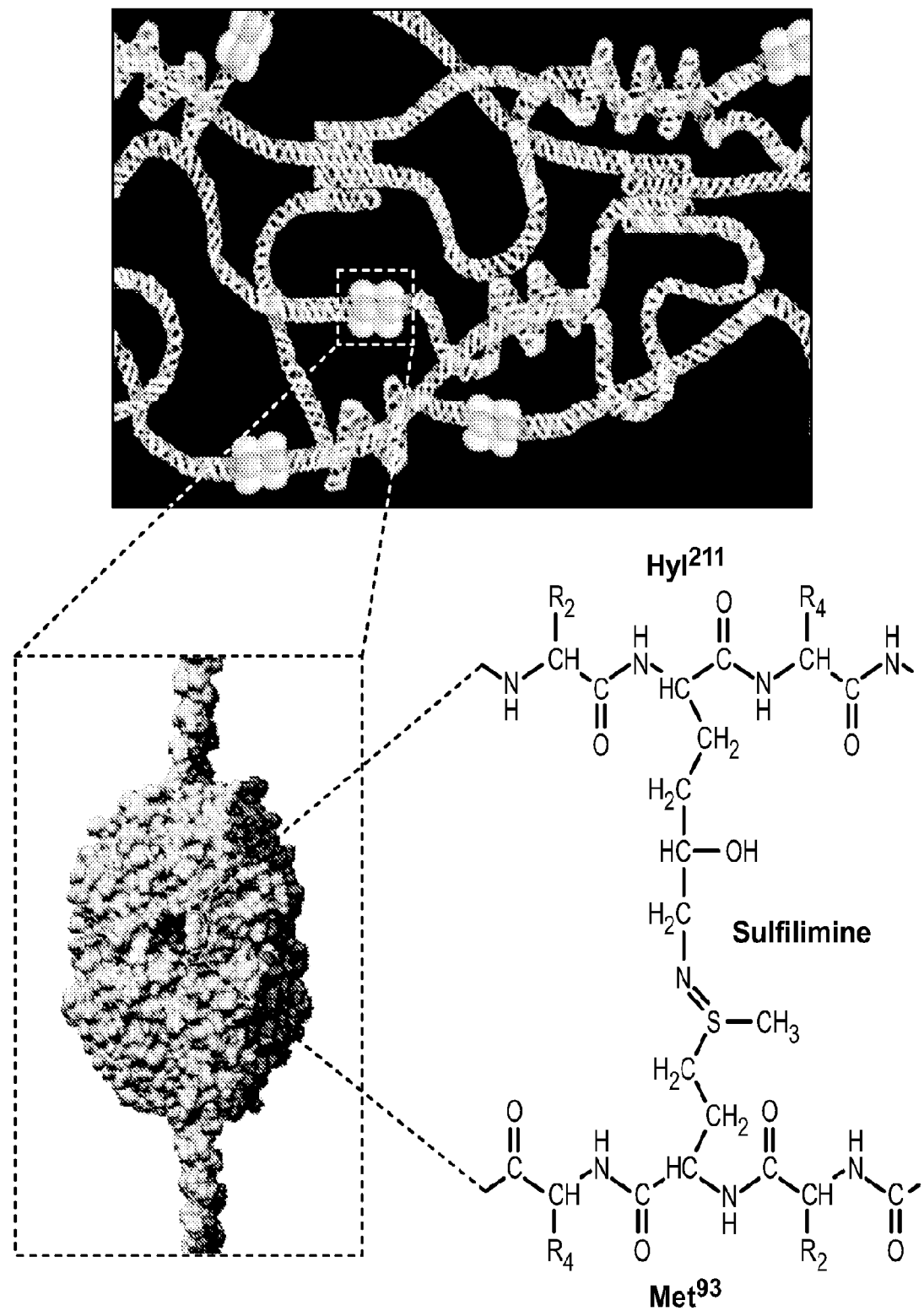
FIG. 3. Proposed chemical structure of the sHM crosslink. Schematic of the α1α2α1 collagen IV network illustrating the interaction between the NC1 domain of triple-helical protomers. A space-filling model of the NC1 hexamer quaternary structure shows the location of the sHM crosslinks (white). The sulfilimine bond that constitutes the sHM crosslink connecting the side chains of $Met^{93}$ and $Hyl^{211}$ is shown.

A sulfilimine bond (Met$^{93}$-S=N-Hyl$^{211}$) has been identified that stabilizes the NC1 trimer-NC1 trimer interaction in which the sulfur atom of methionine-93 residue from one NC1 domain connects to the ε-nitrogen atom of hydroxyl-ysine-211 of an interacting NC1 domain (FIG. 3). This is the first time that a sulfilimine (Met-S=N-Hyl) bond has been described in a protein or a biomolecule. The crystal structure of the NC1 hexamer (Sundaramoorthy et al., 2002) demonstrates that this bond plays a critical role in not only stabilizing the quaternary structure of the NC1 hexameric complex but also as reinforcement to the entire collagen IV network. The inventors have now determined that the enzyme responsible for this bond formation is human peroxidasin (PXDN).

The sulfilimine bond likely occurs in diverse metazoan species. NC1 dimer subunits, a signature structural feature indicative of crosslinks, have been identified in collagenase digests of basement membranes including human (Weber et al., 1984), bovine (Weber et al., 1984), dog (Thorner et al., 1996), and mouse (Weber et al., 1984). Furthermore, a phylogenetic analysis of the Lys$^{211}$ and Met$^{93}$ residues, based on a multiple sequence alignment of the NC1 domain across the metazoan phylum (FIG. 4 and Aouacheria et al., 2006), revealed that the sulfilimine bond may occur in many metazoans, except in hydra, flatworm, sponge, and placozoa. A further comparison of the sequence motif (X-K-A/S/G) that confers hydroxylation of lysyl residues by lysyl hydroxylase (Kivirikko and Pihlajaniemi, 1998) occurs in the NC1 domains of all metazoa except hydra, sponge and placozoa.

The motif is also absent in the α4 NC1 domain of human, mouse, bovine and chick, which in the case of bovine $Lys^{211}$ does not undergo hydroxylation and leads to the formation of s-lysyl-methionine crosslink (Vanacore et al., 2008). In one species of the phylum Cnidaria, *Nematostella vectensis*, both $Met^{93}$ and $Lys^{211}$ and the hydroxylation motif of Lys are conserved (FIG. 4), suggesting that the sHM crosslink appeared at the time of the divergence of sponge and cnidaria, an apparent evolutionary adaptation that arose in response to an increase in mechanical stress on organisms.

The sulfilimine cross-linking of collagen IV may be a molecular step promoting angiogenesis and tumor growth, and provides a means to inhibit cross-link formation and potentially mitigate cancer progression. The sulfilimine bond relationship is also highly relevant to stability in proteins, both as a single polypeptide or in complex of multiple interacting subunits. Therefore, the present invention provides for methods to modulate, including inhibition, of the formation of sulfilimine bonds in various clinical settings, such as cancer.

A. HUMAN PEROXIDASIN AND SULFILIMINE CROSSLINKS

1. Human Peroxidasin

Mammalian peroxidases are heme-containing enzymes that serve diverse biological roles, such as host defense and hormone biosynthesis. A mammalian homolog of *Drosophila peroxidasin* belongs to the peroxidase family. Studies have shown that human peroxidasin is present in the endoplasmic reticulum of human primary pulmonary and dermal fibroblasts, and the expression of this protein is increased during transforming growth factor-β1-induced myofibroblast differentiation (Donkó et al., 2009). Myofibroblasts secrete peroxidasin into the extracellular space where it becomes organized into a fibril-like network and colocalizes with fibronectin, thus helping to form the extracellular matrix. Peroxidasin expression has been shown to be increased in a murine model of kidney fibrosis and that peroxidasin localizes to the peritubular space in fibrotic kidneys.

The accession nos. for human peroxidasin precursor protein and mRNA are NP_036425.1 (SEQ ID NO:29) and NM_012293.1 (SEQ ID NO:30), respectively, which are hereby incorporated by reference.

2. Sulfilimine Crosslinks

The sulfilimine crosslinks play a pivotal role in the function of collagen IV networks and basement membranes; hence, they are an attractive pharmacological target to halt tumor progression by inhibiting the formation of newly developed blood vessels Inhibitor of the formation of sulfilimine crosslinks represent a new class of angiogenic inhibitors for cancer therapy whereby they interfere with the normal mechanism of collagen IV assembly, resulting in inhibition of blood vessel formation and tumor growth.

Using mass spectrometry (MS) analyses of crosslinked tryptic (Tp) peptides and a smaller crosslinked post-proline endopeptidase (PPE) peptides, both derived from the α1α2α1 collagen IV network of placenta, it was found that $Lys^{211}$ is modified to hydroxylysine ($Hyl^{211}$) and that $Hyl^{211}$ is covalently linked to $Met^{93}$ forming a S-hydroxylysyl-methionine (sHM) crosslink. In the α3α4α5 network, it was found that the sHM crosslink connects the α3 and α5 NC1 domains, but the α4 NC1 domains are connected by a S-lysyl-methionine crosslink, involving Lys instead of $Hyl^{211}$, indicating that this post-translational modification is not a requirement for crosslink formation. However, the nature of the bond linking $Met^{93}$ and $Hyl^{211}$ could not be determined previously because the observed difference of one mass unit between the uncrosslinked and crosslinked peptides fell within experimental error.

Figure 1A:
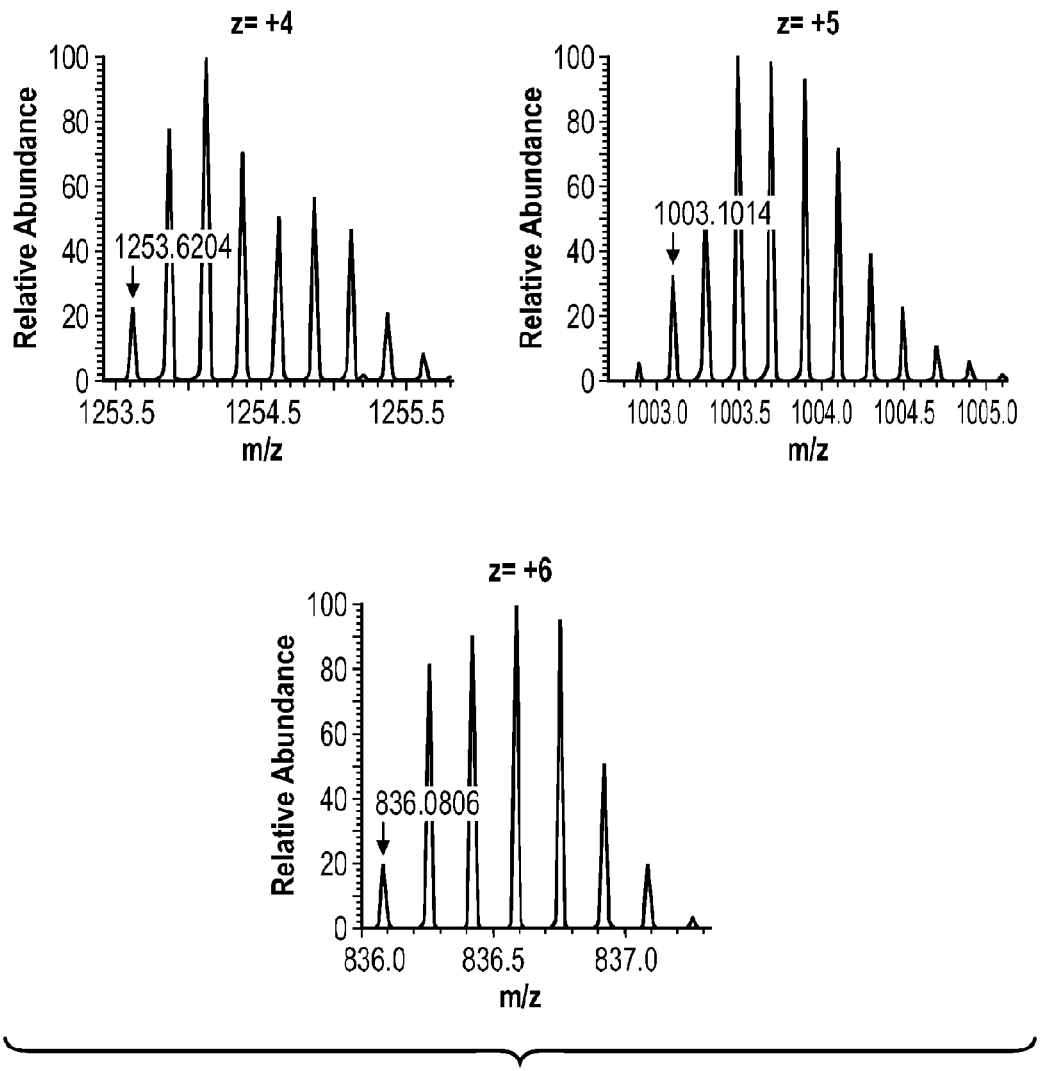
FIGS. 1A-D. MS and NMR analyses of the crosslinked Tp-peptides from the α1α2α1 network.

Herein, the chemical nature of the bond was identified using Fourier transform ion cyclotron resonance (FTICR), which can achieve very high mass accuracy (e.g. <2 ppm, approximately ±0.001 mass units for a peptide with a mass of 5,000), and NMR spectroscopy to analyze crosslinked Tp-peptides. FIG. 1A shows the multiple-charge states (+4, +5, and +6) of the crosslinked Tp-peptide. For each charge state, ten consecutive scans were averaged to obtain the observed monoisotopic mass value of 5010.471±0.022 (FIG. 1A). This value is 2.017 mass units lower than the theoretical total mass (5012.486) of the two constituent tryptic peptides, a $Met^{93}$-containing peptide (T-3599.688) and a $Hyl^{211}$-containing peptide (T-1412.777), which were previously described (Vanacore et al., 2005).

The location of the sulfilimine linkage within the α1α2α1 collagen IV network is shown in FIG. 3. Up to 6 sulfilimine bonds fasten the interface of the trimeric NC1 domains of two adjoining protomers, reinforcing the quaternary structure of the networks. Furthermore, the sulfilimine bond also occurs in the α3α4α5 collagen IV network (FIG. 7) because fragmentation pattern of its crosslinked tryptic peptides (Vanacore et al., 2008) is identical to that of the α1α2α1 network described herein. This sulfilimine linkage between Met and Lys/Hyl may not occur only in collagen IV but in other proteins as well.

B. SYNTHESIS OF THE SULFILIMINE CROSSLINK BOND

In some embodiments, the sulfilimine crosslinks may be synthesized, either chemically or enzymatically, to increase stability of a protein or polymerize a protein. This process may be useful, for example, to network peptides and proteins, or to create a supramolecular complex.

In one embodiment, the sulfilimine crosslink is generated by PXDN enzyme, described above. The enzyme may be admixed with target proteins, or the enzyme may be introduced into a cell by virtue of an expression vector encoding the PXDN gene, where the cell further expresses a target protein for crosslinking.

C. INHIBITION OF FORMATION OF THE SULFILIMINE CROSSLINK BOND

Figure 9:
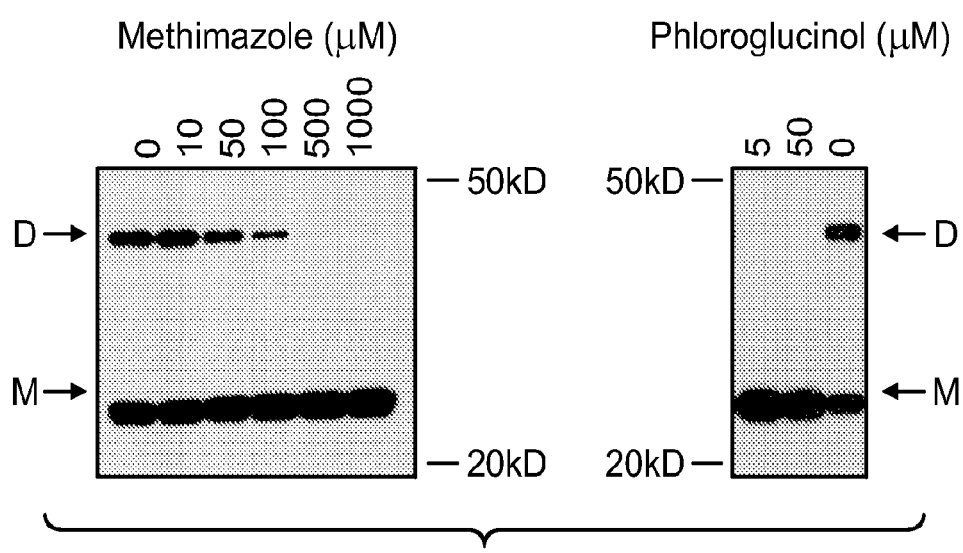
FIG. 9. Methimazole and Phloroglucinol inhibit type IV collagen NC1 domain sulfilimine crosslink formation. NC1 domains were prepared from collagenase digests of extracellular matrix derived from cultured PF HR9 mouse endodermal cells and detected by western blotting with an anti-α2 chain monoclonal antibody. Left panel, Increasing concentrations of Methimazole decreases crosslinked NC1 dimer (D) while increasing non-crosslinked monomer (M). Right panel, Phloroglucinol inhibits dimer (D) formation more potently with near complete inhibition at 5 uM and complete inhibition at 50 uM.

Experimental evidence shows that the formation of sulfilimine crosslinks is an enzymatic-driven process that takes place in the extracellular matrix. In a cell culture system shown to produce native type IV collagen, it has been found that the peroxidase inhibitors methimazole and phloroglucinol inhibit cross-link formation (FIG. 9). While these inhibitors are specific for any peroxidase system, the data demonstrate that cross-link formation in the extracellular matrix can be pharmacologically manipulated. Standard drug discovery strategies may identify other agents that specifically target the sulfilimine cross-link system with minimal inhibition of other peroxidase systems. In addition, a monoclonal antibody can be generated to inhibit enzyme activity. These agents represent anti-angiogenic oncologic agents that can be translated to clinical medicine with broad application.

With the identification of PXDN as the responsible enzyme, additional methods of interfering with enzyme function are available. For example, monoclonal antibodies to PXDN exist that can be used to block function. Similarly, peptides of PXDN can be used to intefere, e.g., with PXDN substrate recognition. Also, antisense nucleic acids and interfering RNAs (siRNA, miRNAs, shRNAs, agRNA) that correspond to or are homologous to the PXDN coding region, introns, exons, intron/exon junctions, promoters, transcriptional start sites, or 3'UTR may be used to modulate function.

D. DISEASE STATES

1. Angiogenesis and Cancer

In some embodiments, the sulfilimine crosslink inhibitor inhibits angiogenesis. Angiogenesis is a physiological process involving the growth of new blood vessels from pre-existing vessels. It is an important physiological process, without which embryonic development and wound healing would not occur. However, excessive or inappropriate angiogenesis is associated with a number of diseases, conditions, and adverse treatment results.

Examples of disease types and conditions associated with excessive angiogenesis include inflammatory disorders such as immune and non-immune inflammation, rheumatoid arthritis, chronic articular rheumatism and psoriasis; disorders associated with inappropriate or inopportune invasion of vessels such as diabetic retinopathy, neovascular glaucoma, retinopathy of prematurity, macular degeneration, corneal graft rejection, retrolental fibroplasia, rubeosis, capillary proliferation in atherosclerotic plaques and osteoporosis; and cancer associated disorders, including for example, solid tumors (pancreatic, colon, testicular, ovarian, uterine, lung, breast, skin, brain, stomach, esophageal, tracheal, head & neck, bone, liver), tumor metastases, blood born tumors such as leukemias, angiofibromas, Kaposi sarcoma, benign tumors such as hemangiomas, acoustic neuromas, neurofibromas, trachomas, and pyogenic granulomas, as well as other neoplasms which require neovascularization to support growth. Additional examples of angiogenesis-dependent diseases include, for example, Osler-Webber Syndrome; myocardial angiogenesis; plaque neovascularization; telangiectasia; hemophiliac joints and wound granulation. Furthermore, excessive angiogenesis is also associated with clinical problems as part of biological and mechanical implants (tissue/organ implants, stents, etc.). The instant compositions can be used to inhibit angiogenesis, and thus in the treatment of such conditions. Other diseases in which angiogenesis plays a role, and to which the instant compounds and compositions can be used, are known by those of skill in the art.

2. Other Diseases

Other diseases that may involve the sulfilimine bond include diseases caused by a helminth infection. Parasitic worms or helminths are a division of eukaryotic parasites that, unlike external parasites such as lice and fleas, live inside their host. Helminth infections include ascariasis, dracunculiasis, elephantiasis, hookworm, lymphatic filariasis, onchocerciasis, schistosomiasis, and trichuriasis. The sulfilimine bond potentially is required for development of these helminths. In such diseases, the use of a sulfilimine crosslink inhibitor may be used to inhibit the development of these helminths and to treat the disease.

Perturbation of an enzymatic process that catalyzes the formation of these sulfilimine links can also be the basis for immune diseases. For example, in Goodpasture autoimmune disease, crosslinks in the $\alpha3\alpha4\alpha5$ network confer molecular immune privilege to the autoantigen (Vanacore et al., 2008; Borza et al., 2005). Loss of privilege could occur by inhibition of the crosslinking enzyme by toxic chemicals, triggering an autoimmune response.

E. PHARMACEUTICAL FORMULATIONS AND ROUTES OF ADMINISTRATION

The inhibitors of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the inhibitor by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The inhibitor may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The inhibitor can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

The actual dosage amount of an inhibitor of the present disclosure or composition comprising an inhibitor of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1,000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending, of course, of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range, for example, of 750 mg to 9,000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 microgram/kg/body weight, about 5 microgram/kg/body weight, about 10 micro-gram/kg/body weight, about 50 microgram/kg/body weight, about 100 micro-gram/kg/body weight, about 200 microgram/kg/body weight, about 350 micro-gram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1,000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc.

F. COMBINATION THERAPY

In addition to being used as a monotherapy, the inhibitors of the present disclosure may also find use in combination therapies. Effective combination therapy may be achieved with a single composition or pharmacological formulation that includes both agents, or with two distinct compositions or formulations, at the same time, wherein one composition includes a compound of this invention, and the other includes the second agent(s). Alternatively, the therapy may precede or follow the other agent treatment by intervals ranging from minutes to months.

Various combinations may be employed, such as when a sulfilimine modulator is "A" and "B" represents a secondary agent, non-limiting examples of which are described below:

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the inhibitors of the present disclosure to a patient will follow general protocols for the administration of pharmaceuticals, taking into account the toxicity, if any, of the drug. It is expected that the treatment cycles would be repeated as necessary.

For the treatment or prevention of cancer, modulators of the present invention may be combined with one or more of the following: radiation, chemotherapy agents (e.g., cytotoxic agents such as anthracyclines, vincristine, vinblastin, microtubule-targeting agents such as paclitaxel and docetaxel, 5-FU and related agents, cisplatin and other platinum-containing compounds, irinotecan and topotecan, gemcitabine, temozolomide, etc.), targeted therapies (e.g., imatinib, bortezomib, bevacizumab, rituximab), or vaccine therapies designed to promote an enhanced immune response targeting cancer cells.

G. EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Identification of the Sulfilimine Bond

Figure 1B:
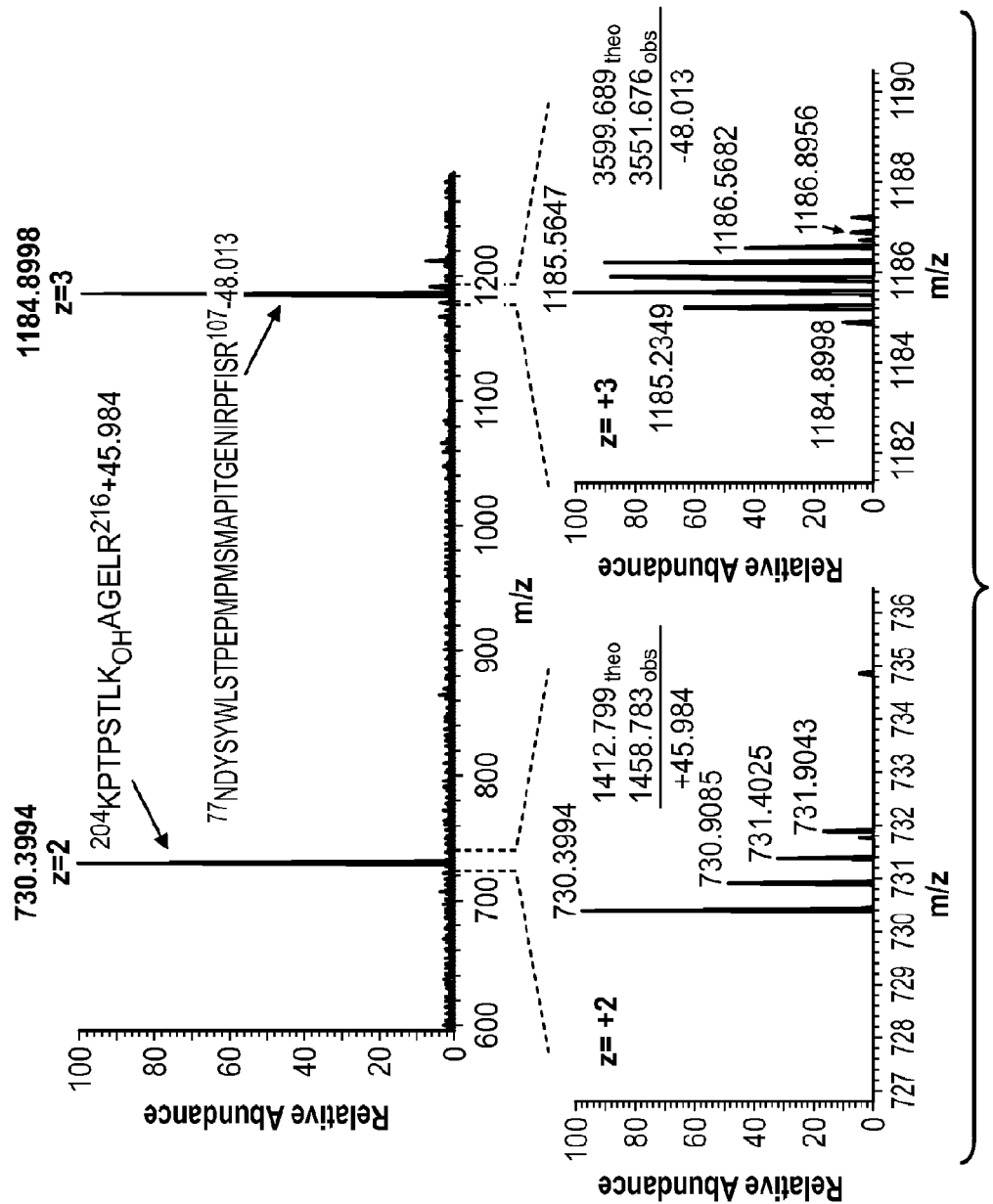
Figure 5A:
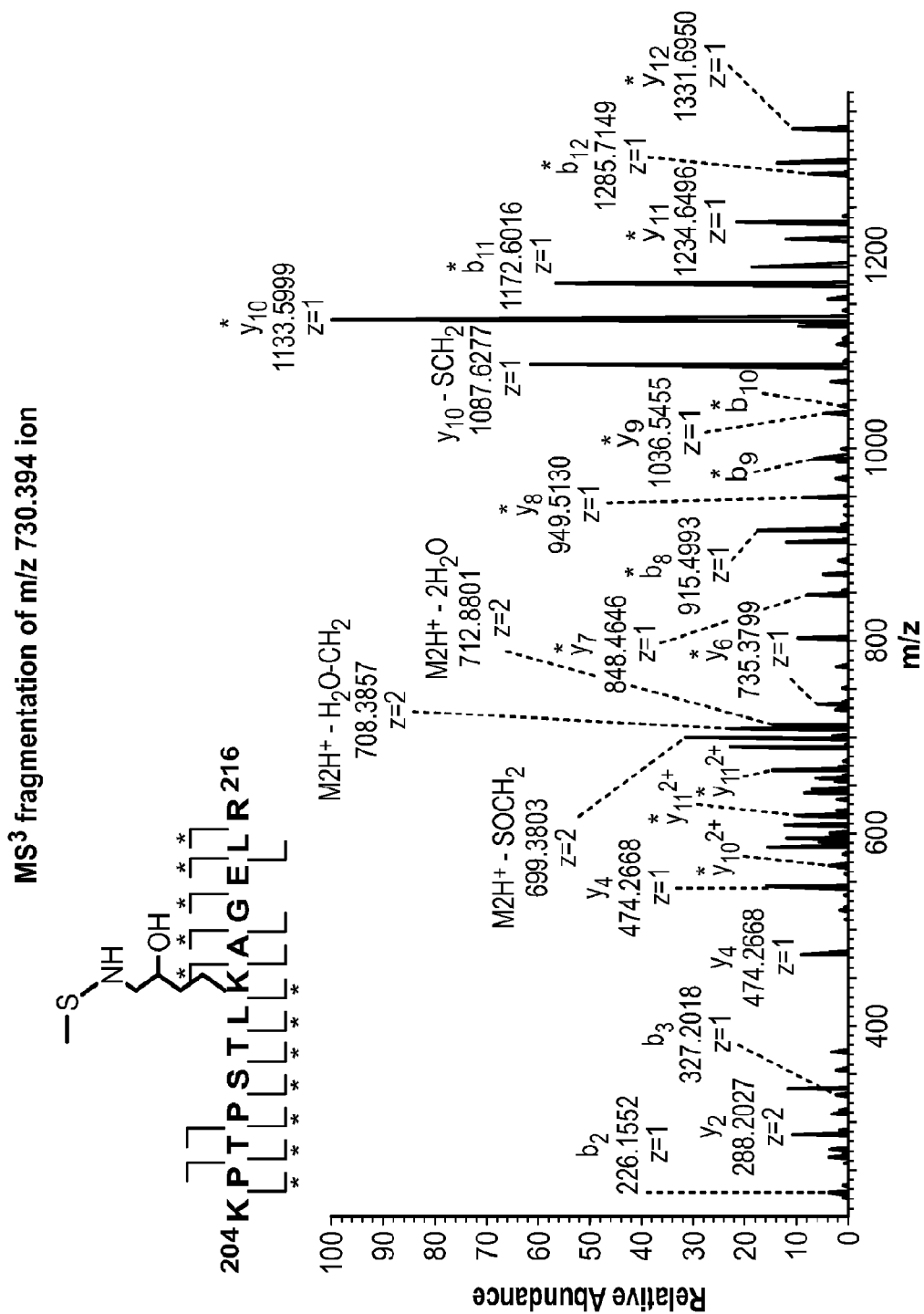
FIGS. 5A-B. Characterizatin of mass changes to specific residues within the Tp-peptide sequences. The m/z 730.394 and m/z 1184.900 ions were selected for higher order CID fragmentation (e.g., FTICR-MS$^3$).
Figure 5B:
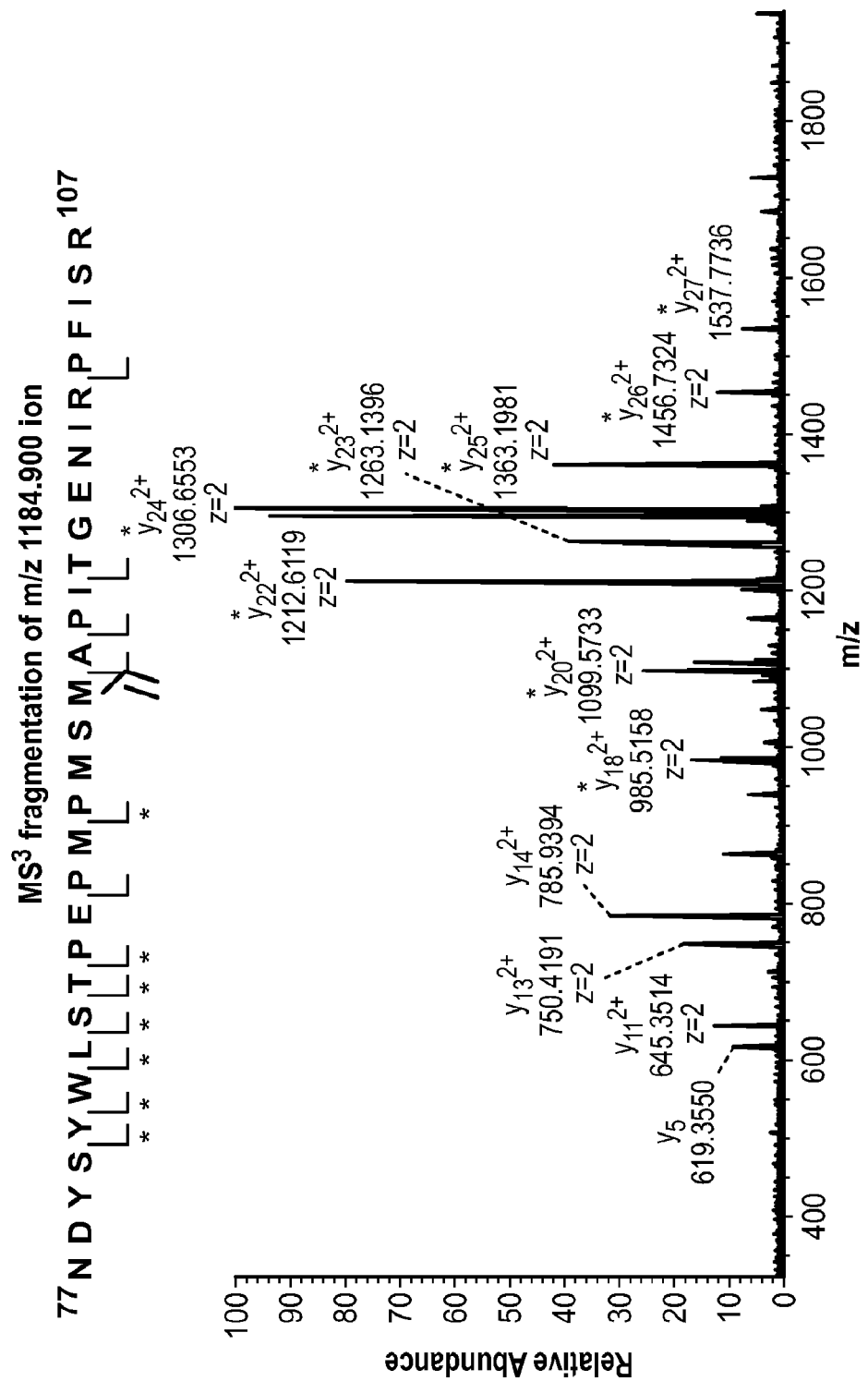
Figure 6A:
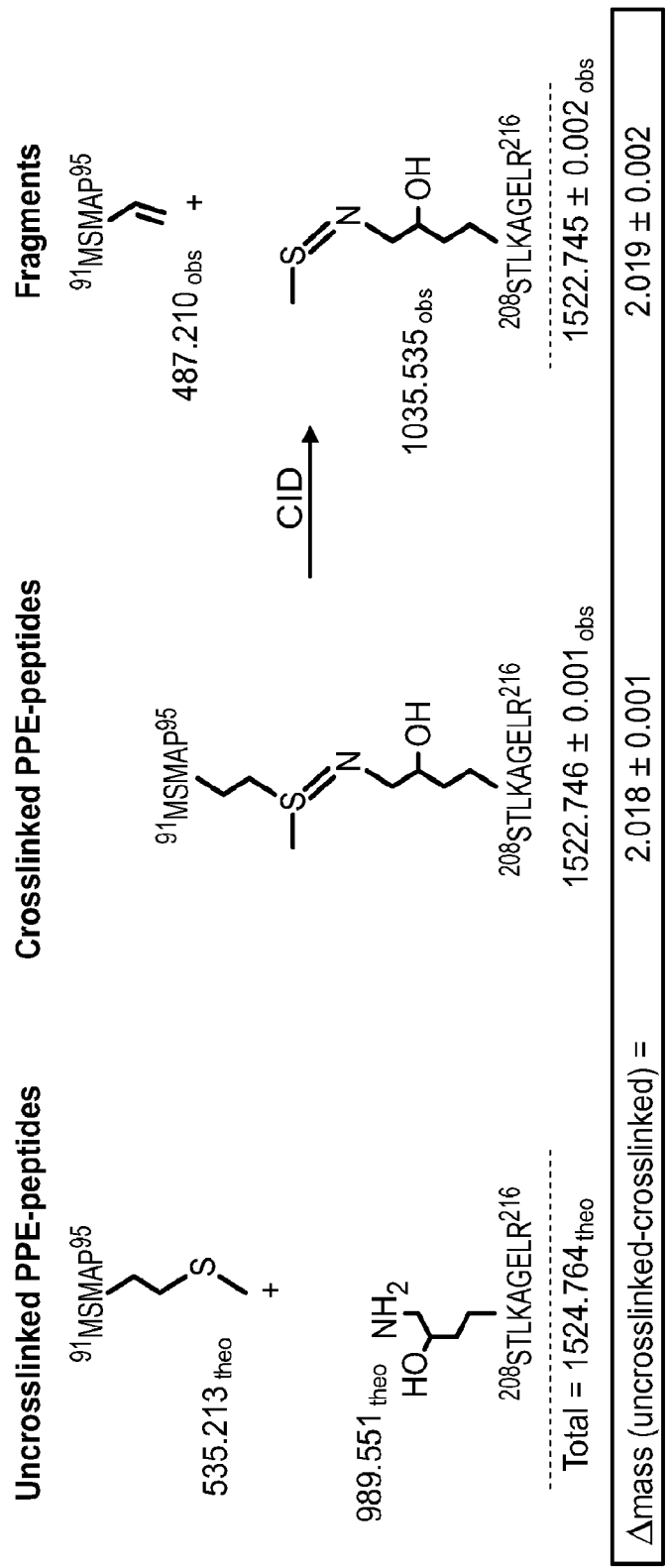
FIGS. 6A-E. Confirmation of two proton loss. T-5014 complex was further digested with post-proline endopeptidase to reduce its size to P-1525 complex and the mass measurements with the ESI-FTICR-MS instrument were performed (SEQ ID NOS: 27 and 28).
Figure 6B:
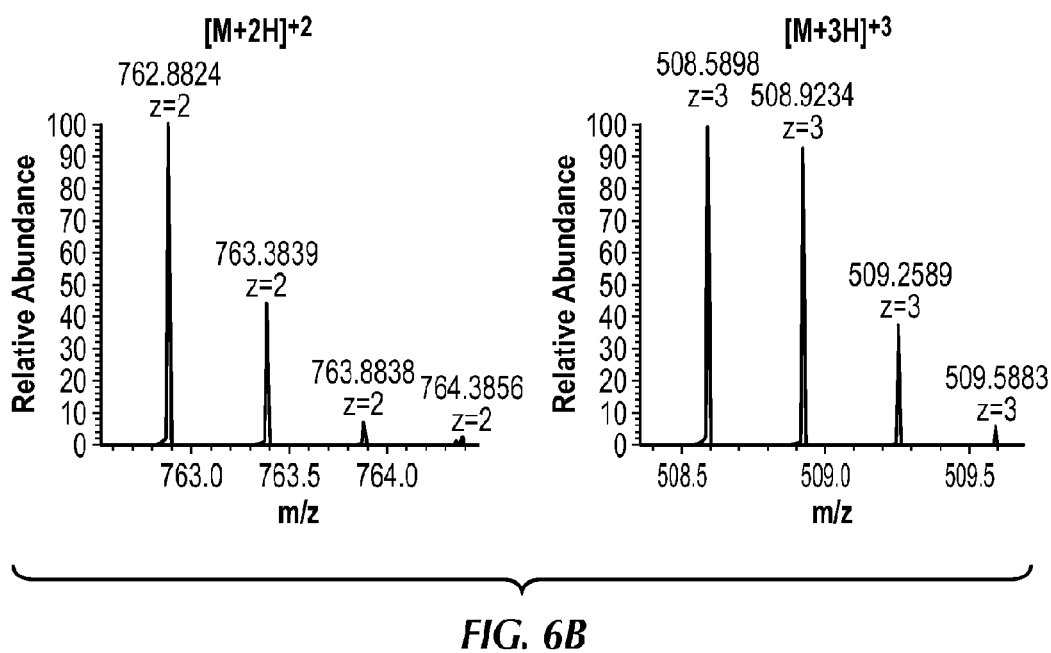
Figure 6C:
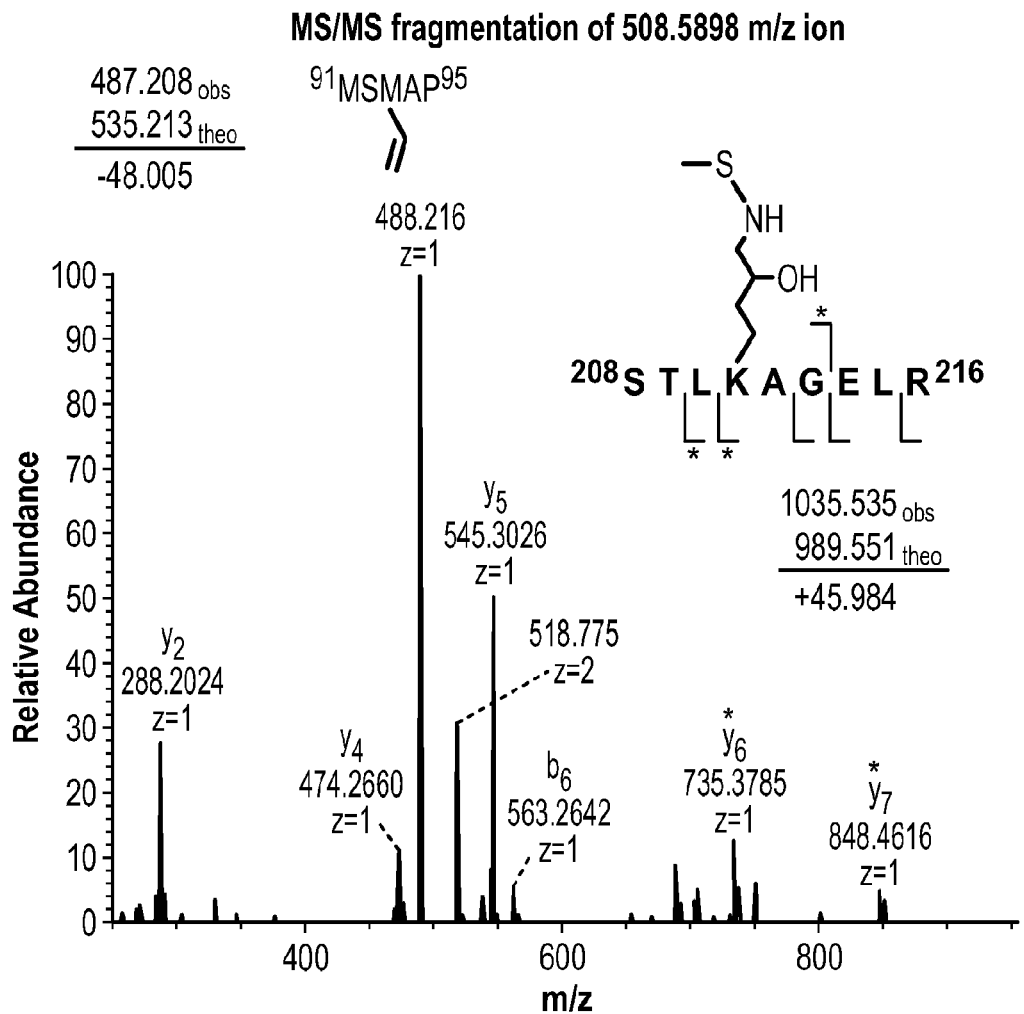
Figure 6D:
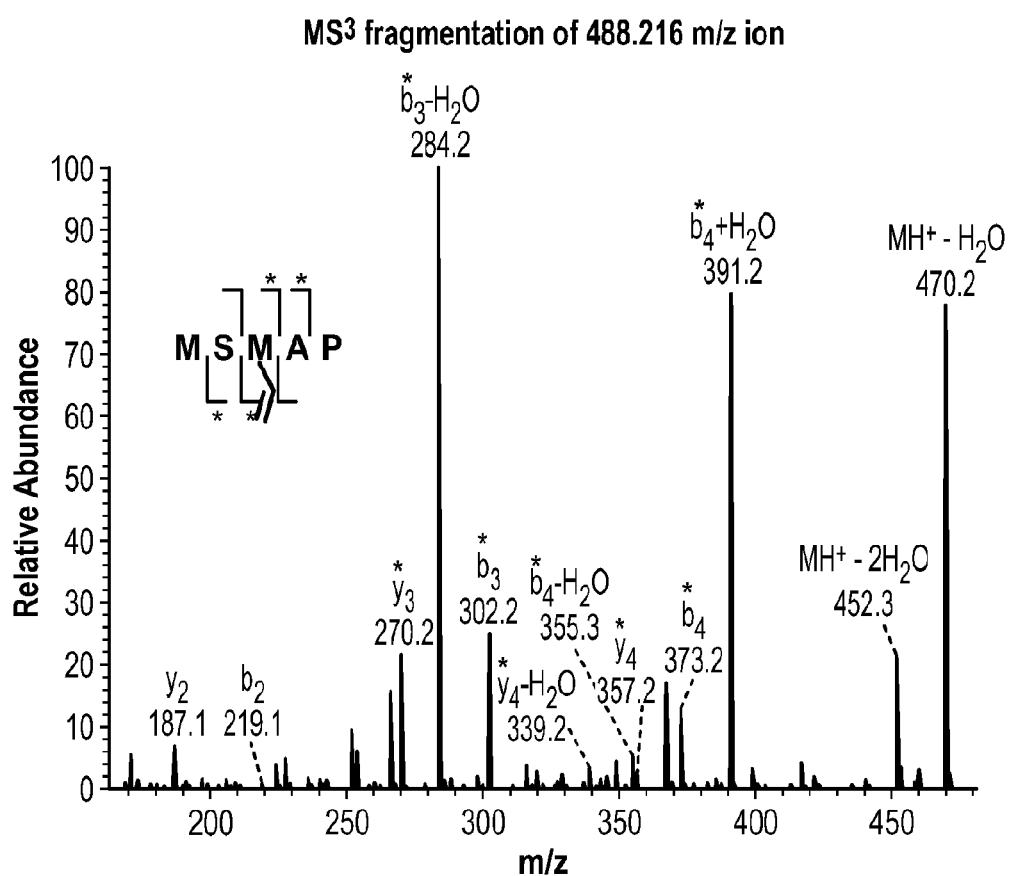
Figure 6E:
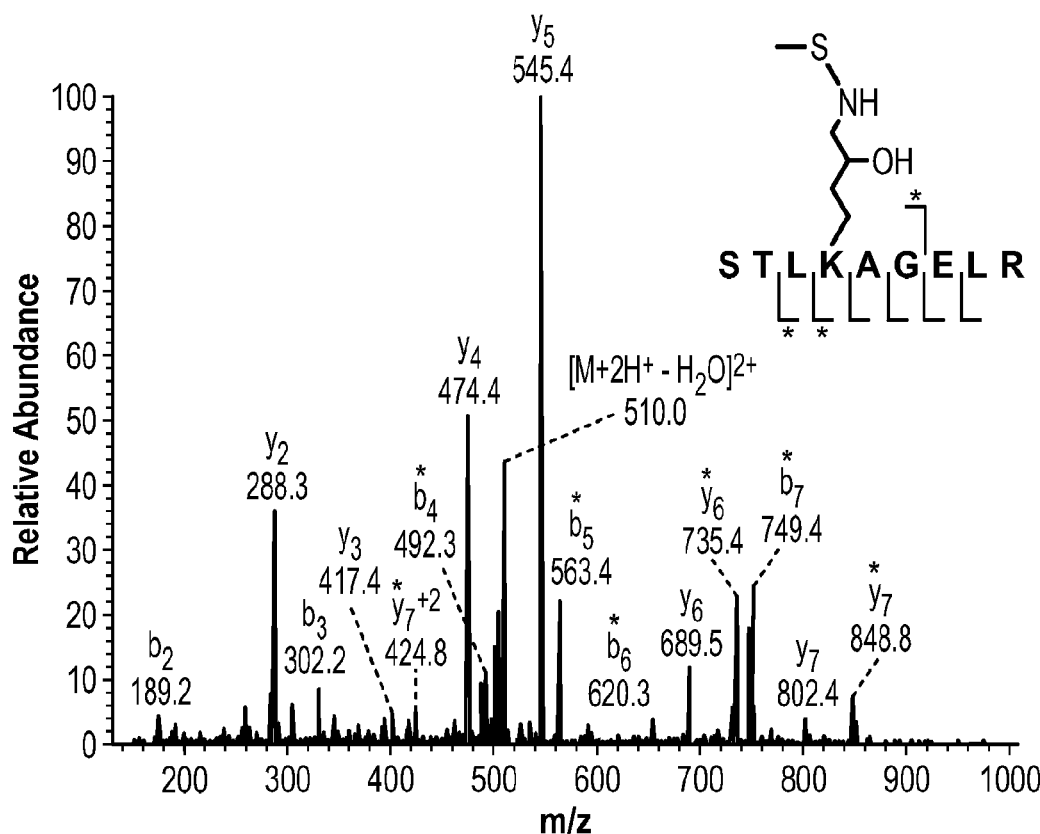

To determine the location of modifications that lead to the loss of 2.017 mass units, the tryptic complex was analyzed by collision-induced dissociation (CID) MS$^3$ fragmentation analysis. The m/z 1003.1014 (+5) ion was selected for MS$^2$ fragmentation, which generated a m/z 730.3994 ion, corresponding to the T-1412.799 peptide plus 45.984 mass units and a m/z 1184.900 ion, corresponding to the T-3599.689 peptide that lost 48.013 mass units (FIG. 1B). To locate these mass changes to specific residues, the m/z 730.3994 and 1184.900 ions were selected for further CID (MS$^3$). The y- and b-series of the spectra confirm not only the sequence of the T-1412.799 peptide, but also that the location of the mass change of +45.984 corresponds to the side chain of Hyl$^{211}$ (FIG. 5A). The MS$^3$ fragmentation profile for the m/z 1184.900 ion also verified the peptide sequence, and localized the loss of 48.013 mass units to Met$^{91}$ or Met$^{93}$ (FIG. 5B). The MS$^3$ fragmentation profile for the m/z 1184.900 ion also verified the peptide sequence, and localized the loss of 48.013 mass units to Met$^{91}$ or Met$^{93}$ (FIG. 5B). A smaller crosslinked PPE-peptide complex derived from the crosslinked Tp-peptides (FIG. 6) confirmed that the loss of 48.013 mass units is localized to the side chain of Met$^{93}$. An analogous fragmentation has been observed in methionine sulfoxide containing peptides that undergo concomitant neutral loss of methane sulfenic acid ($CH_3SOH$) (Lagerwerf et al., 1996; Reid et al., 2004). In this case, however, this group remains attached to the side chain of Hys$^{211}$, demonstrating the covalent nature of the interaction between Met$^{93}$ and Hyl$^{211}$.

Figure 1C:
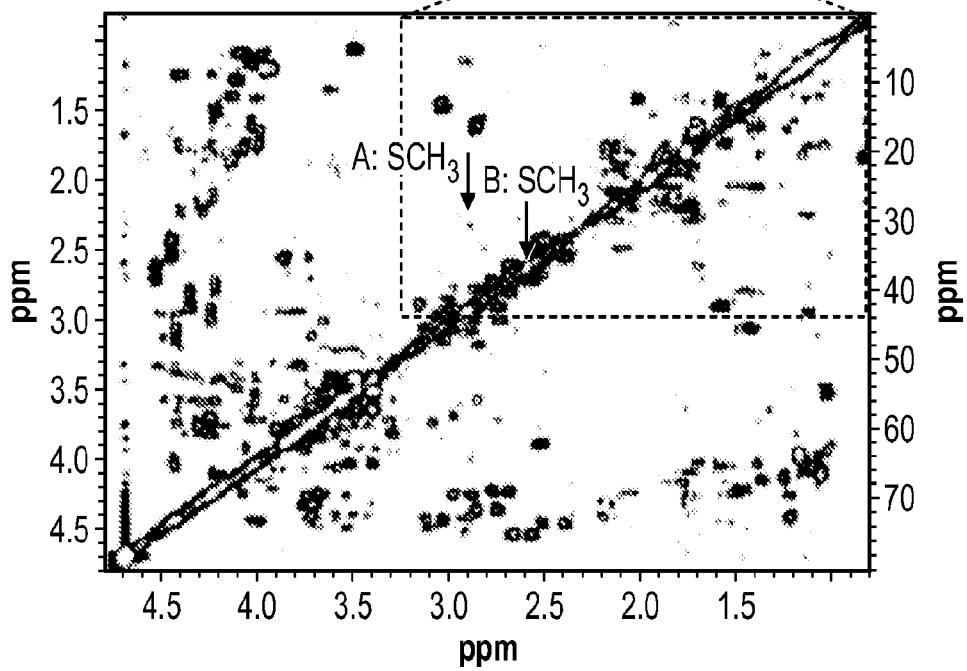
Figure 1D:
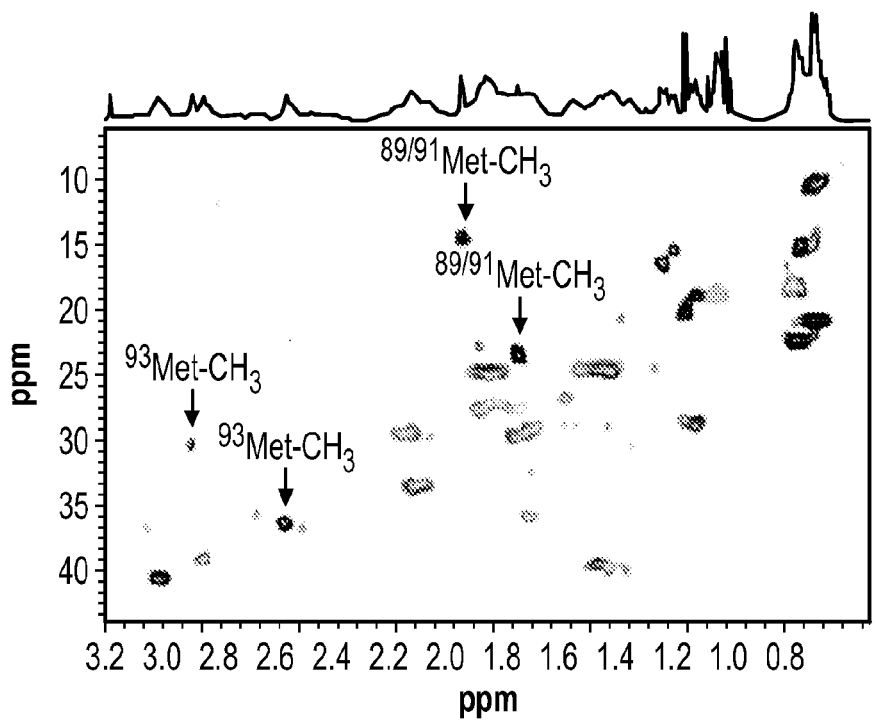

An overlay of correlation spectroscopy (COSY) and heteronuclear multiple quantum correlation ($^1$H-$^{13}$C HMQC) spectra of the crosslinked Tp-peptides was used to evaluate the chemical shift of the methyl group of Met$^{93}$ (FIG. 1C). The sequences of crosslinked Tp-peptides have a total of 25 methyl groups, 3 of which belong to Met$^{89}$, Met$^{91}$, and Met$^{93}$. Typical proton chemical shift for methyl groups in peptides of Leu, Thr, Iso and Ala is between 0 and 1.5 ppm, and that of methionine is about 2.1 ppm. Eighteen out of 22 total methyl groups of Leu, Thr, Ile, and Ala were identified within the expected chemical shift range in the HMQC spectrum (data not shown). An edited HSQC analysis was carried out to identify the methyl groups of Met$^{89}$, Met$^{91}$, and Met$^{93}$. In the chemical shift range expected for Met, two signals were observed; one at $^1$H 1.9 ppm/$^{13}$C 14 ppm and the other at $^1$H 1.7/$^{13}$C 24 ppm, presumably correspond to Met$^{89}$ and/or Met$^{91}$, (FIG. 1D). In addition, two downfield-shifted methyl resonances were observed with atypical chemical shifts at $^1$H 2.9 ppm/$^{13}$C 30 ppm and $^1$H 2.6 ppm/$^{13}$C 36 ppm. These likely correspond to the methyl group of Met$^{93}$ in two different chemical environments.

Figure 2A:
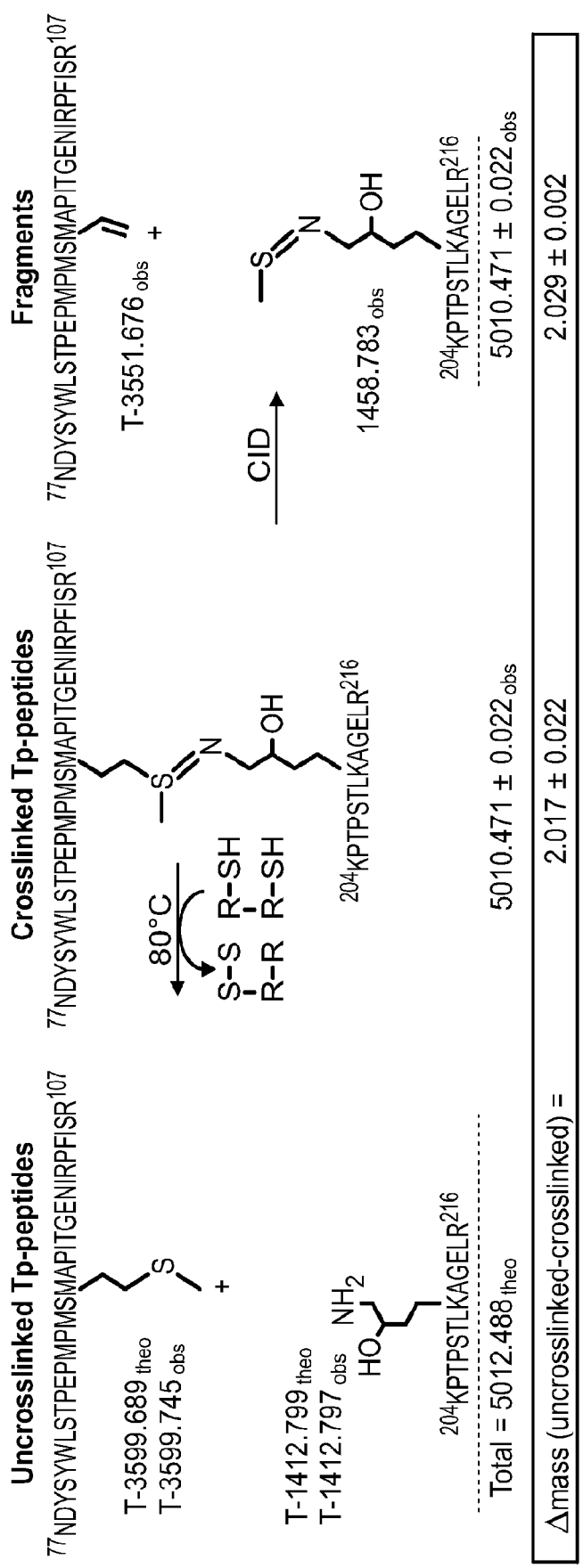
FIGS. 2A-B. Summary of the MS analyses of the crosslinked Tp-peptides before and after reduction with DTT.

The collective evidence from the MS and NMR indicates the existence of a sulfilimine bond in the crosslinked Tp-peptides (FIG. 2A). Mass spectrometry analysis revealed that the linkage between Met$^{93}$ and Hyl$^{211}$ is characterized by the loss of two hydrogen atoms, which is consistent with oxidation resulting in a double bond connecting the sulfur atom of Met$^{93}$ and the nitrogen atom of Hyl$^{211}$ (FIG. 2A). The MS$^2$ fragmentation of the tryptic complex can be explained by a concerted process in which a β-hydrogen is taken up by the nitrogen leading to the cleavage of the bond between sulfur and γ-carbon of Met$^{93}$ (Cope elimination) (Cope et al., 1960). The resulting products are shown in FIG. 2A. The sulfilimine structure is further supported by a down-shifted methyl peak in the NMR spectrum of the crosslinked Tp-peptides, which is consistent with the shift of the methyl group of S-methyl-isothiazolidinium nitrate ($^1$H 2.78 ppm). Although a sulfilimine bond has not been reported in any native biomolecule, they occur in other molecules. They are the nitrogen analog of sulfoxides, S(IV), and are also known as sulfur-nitrogen ylides. Most sulfilimines in the literature are stabilized by strong electron withdrawing groups adjacent to the sulfilimine linkage (Gilchrist and Moody, 1977), however, cyclic sulfilimines derived from the oxidation of methionine analogs by 12 have been characterized in detail as their isothiazolidinium salts following protonation of the nitrogen (Lambeth and Swant, 1979; Glass and Duchek, 1976). These studies showed direct bonding of the nitrogen and sulfur atoms and a new chiral center at the sulfur atom.

Figure 2B:
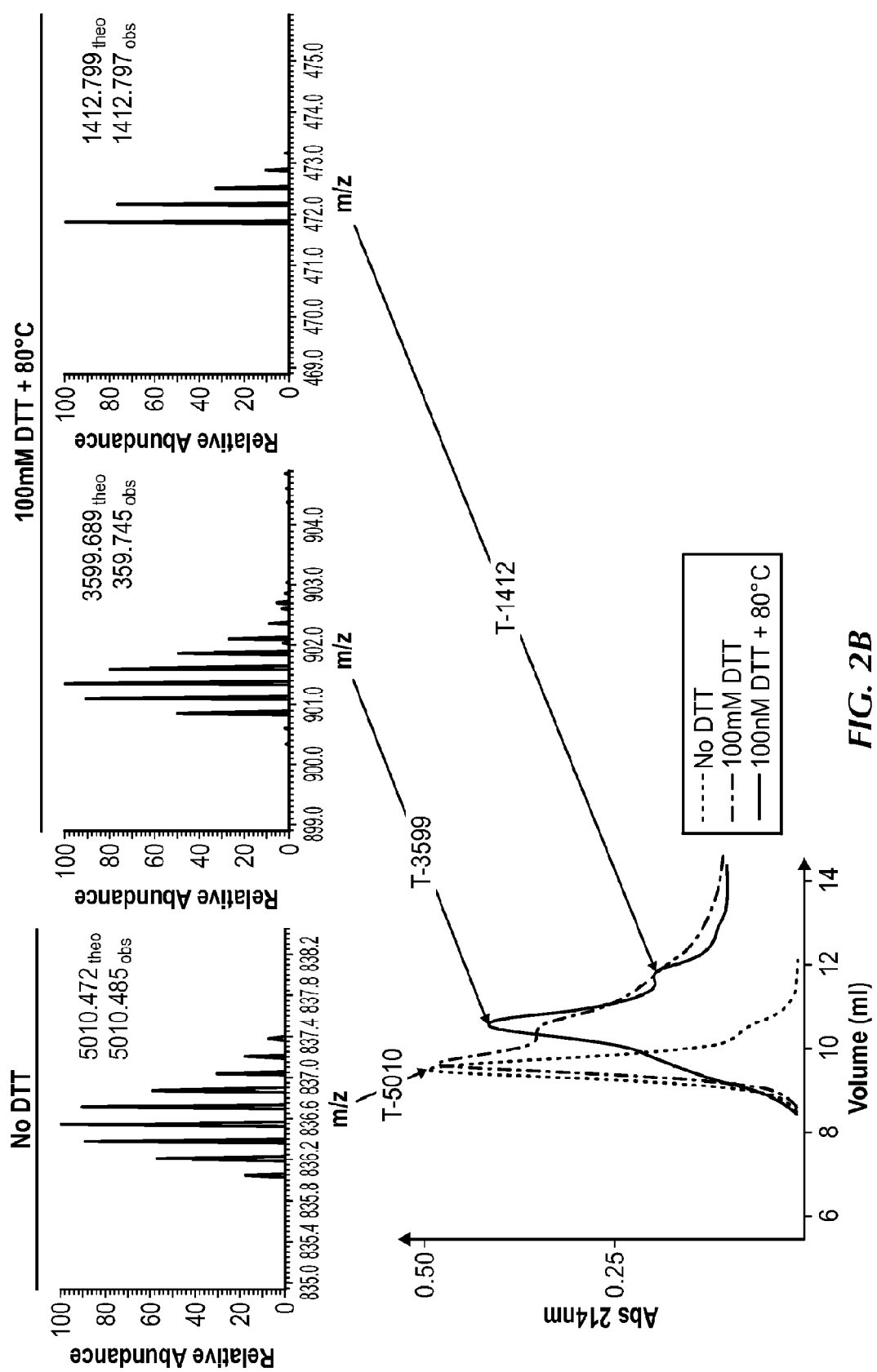
Figure 7:
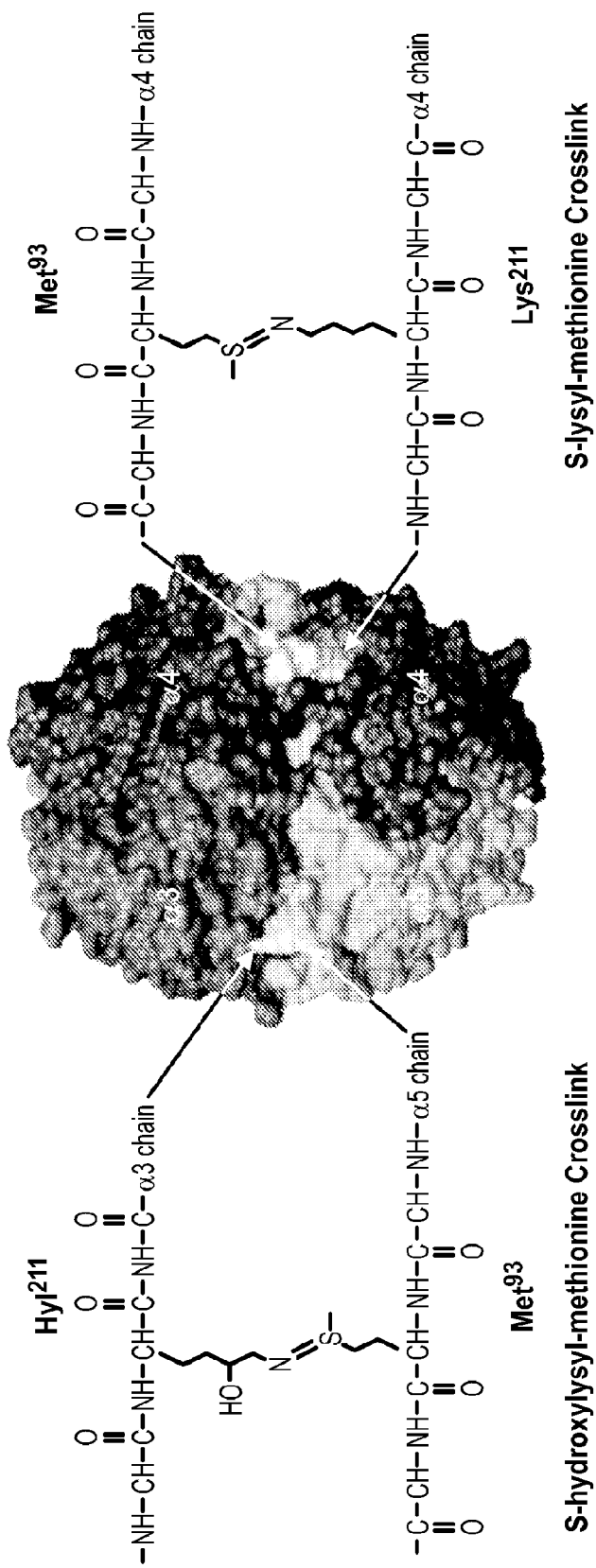
FIG. 7. The bond in both the sHM and sKM crosslinks of the α3α4α5 collagen IV network is a sulfilimine.

Sulfilimines are reduced by thiols to yield the parent amine and thioether groups (Gilchrist and Moody, 1977). Thus, the susceptibility of the crosslinked Tp-peptide to dithiothreitol (DTT) reduction was evaluated (FIG. 2B). Partial reduction was achieved with 100 mM DTT at room temperature and complete reduction at 80° C. at pH 7.8. Mass spectrometry analyses revealed that DTT breaks the crosslink with the concomitant generation of the T-3599 and T-1412 peptides with complete recovery of both Met$^{93}$ and Hyl$^{211}$, respectively (FIGS. 2A and 2B). The susceptibility of the crosslink to reduction is comparable to that of disulfide bonds of insulin (FIG. 7). Since the crosslinked Tp-peptides do not contain cysteines (FIG. 1A), these results provide further support for the existence of a sulfilimine bond between Hyl$^{211}$ and Met$^{93}$.

Example 2

Materials and Methods

Materials. Bovine placentas were purchased from Pel-Freeze biologicals (Rodgers, A R). Bacterial collagenase (CLSPA) was purchased from Worthington (Lakewood, N.J.).

Isolation of the Crosslinked Tp Peptides.

NC1 dimers (reduced and alkylated) were isolated from bovine placenta NC1 hexamers (PBM hexamers) as described in Vanacore et al. (2005). Purified NC1 dimers were incubated with sequencing grade modified trypsin (Promega, Madison, Wis.) at approximately 1:25 enzyme to protein ratio at room temperature for 16 hours. The crosslinked Tp-peptides were obtained by fractionating the dimer tryptic digest through a Superdex™ peptide column (Amersham Biosciences, Piscataway, N.J.) as described by Vanacore et al. (2005).

Truncation of the Crosslinked Tp-Peptides with Post-Proline Endopeptidase.

The purified crosslinked Tp-peptides were further truncated with post-proline endopeptidase (PPE) from *Flavobacterium meningsepticum* (Seikagaku America, East Falmouth, Mass.) in 0.1 M ammonium bicarbonate pH ~7.8 for 3 hrs at 37° C. The products of the digestion were immediately analyzed by FT-ICR-MS$^3$ (vide infra).

LTQ-FTICR Mass Spectrometry.

Mass measurements of peptide mixtures were performed on a LTQ-FT mass spectrometer (Thermo Electron, San Jose, Calif., USA) 7 Tesla in the positive ion mode. The instrument was fully calibrated prior to all measurements according to the manufacturer's instructions. Mass accuracy of <2 ppm and a nominal resolution of 100,000 were used in acquisition of peptide MS spectra. The automated gain control (AGC) ion targets were set to value 750,000 for full scan, 500,000 for MS/MS and 50,000 for selected ion monitoring (SIM). Capillary temperature was 160° C., Electrospray ionization (ESI) voltage was 1.2 kV, ESI nanoflow tips: PicoTip Emitters from New Objective.

Bioinformatics.

Proteins were identified using a cluster version of the SEQUEST algorithm (Yates et al., 1995) and the SEQUEST Browser software in the Bioworks 3.1 software package (Thermo Electron, San Jose, Calif.), using the bovine subset of the Uniref100 database.

Reducibility of Crosslinked Tp-Peptides.

The crosslinked Tp-peptides, isolated as described above, and Insulin (Sigma-Aldrich) were each resuspended in 0.1 M ammonium bicarbonate pH ~7.8 buffer. Dithiotheritol (DTT) was added to achieve a final concentration of 100 mM from a concentrated stock solution freshly prepared. Samples requiring heating at 80° C. were placed in a water bath for the 15 min and then analyzed by gel filtration chromatography using the Superdex™ peptide column connected to an AKTA purifier HPLC system. Fractions containing the peaks of interest were collected and analyzed by FTMS using an Orbitrap-LTQ mass spectrometer (Thermo Electron, San Jose, Calif.).

LC Separations.

A capillary column (100 μm×11 cm) was filled with C18 resin (Jupiter C18, 5 micron, 300 angstrom, Phenomenex, Torrence Calif.) and a precolumn (100 μm×6 cm) was packed with the same C18 resin using a frit generated with from liquid silicate Kasil 1 (Cortez et al., 1987) similar to that previously described (Licklider et al., 2002), except the flow from the HPLC pump was split prior to the injection valve. The separation occurred at a flow rate of 700 nL/min. The gradient was formed with mobile phase A, 0.1% formic acid, and mobile phase B, acetonitrile with 0.1% formic acid. A 95 min gradient was performed with a 15 min washing period (100% A for the first 10 min followed by a gradient to 98% A at 15 min) to allow for solid phase extraction and removal on any residual salts. After the initial washing period, a 60 minute gradient was performed where the first 35 min was perform a slow, linear gradient from 98% A to 75% A, followed by a faster gradient to 10% A at 65 min and an isocratic phase at 10% A to 75 min.

LTQ-Orbitrap Mass Spectrometry.

ThermoFinnigan LTQ-Orbitrap, MicroAS, Surveyor HPLC pump, Nanospray source, and Xcalibur 1.4 instrument control. The mass spectrometer was tuned prior to analysis using the synthetic peptide TpepK (AVAGKAGAR (SEQ ID NO:1)), so that some parameters may have varied slightly from experiment to experiment, but typically the tune parameters were as follows: spray voltage of 2 kV, a capillary temperature of 150° C., a capillary voltage of 50 V and tube lens of 120 V. The AGC target value was set at 100,000 for the full MS and 10,000 for the MS/MS spectra.

A full scan obtained for eluting peptides in the range of 400-2000 mass units was collected on the Orbitrap portion of the instrument at a resolution of 60,000, followed by three data-dependent MS/MS scans on the LTQ portion of the instrument with a minimum threshold of 1,000 set to trigger the MS/MS spectra. MS/MS/MS were recorded by a data-dependent manner. All spectra were recorded using dynamic exclusion of previously analyzed precursors for 60 s with a repeat of 1 and a repeat duration of 1 min.

NMR Spectroscopy.

$^1$H-$^{13}$C HMQC and HSQC experiments were used to examine the cross-link on the T-5012.799 peptide complex. Experiments were performed on a 500.13 MHz AVANCE spectrometer (Bruker BioSpin, Rheinstetten, Germany) equipped with a triple resonance inverse cryogenically cooled NMR probes $^1$H[$^{13}$C,$^{15}$N]. Purified, natural abundance peptide complex was dissolved in 500 μl D$_2$O in the presence of 50 mM sodium phosphate buffer at pH 7.0, yielding a 0.4 mM solution. The temperature was controlled at 20±0.1° C. Chemical shifts were referenced to the water resonance at 4.82 ppm at 20° C.

The 1D spectrum utilized presaturation to minimize any residual H$_2$O signals. A total of 16394 complex data points were recorded with a sweep width of 6510 Hz and 256 scans. The data was processed with a 90 degree shifted, squared sinebell function.

NMR Two-Dimensional Techniques.

Two-dimensional techniques included standard $^1$H-$^{13}$C HMQC (Palmer et al., 1991), HSQC (Kay et al., 1992; Schleucher et al., 1994) and edited HSQC (Willker et al., 1993), measurements utilizing the sensitivity enhancement in the phase sensitive, echo/antiecho-TPPI mode with gradient and multiplicity selection where applicable and garp4 carbon decoupling during evolution and acquisition (Palmer et al., 1991; Kay et al., 1992; Schleucher et al., 1994; Willker et al., 1993). Typical acquisition parameters were: spectral width of 13 ppm, 1024 complex points in the $^1$H dimension, 80 ppm with 192 to 256 complex points in the $^{13}$C dimension, adiabatic inversion pulses and a relaxation delay of 1.5 s. The JCH delay was optimized to 145 Hz. Data was processed using Bruker software, Topspin 2.0. The data was zero-filled and a 90 degree shifted, squared sinebell function was applied in both dimensions resulting in 2048×1024 spectra matrix.

Involvement of Sulfilimine Crosslinks in Cancers.

Figure 8:
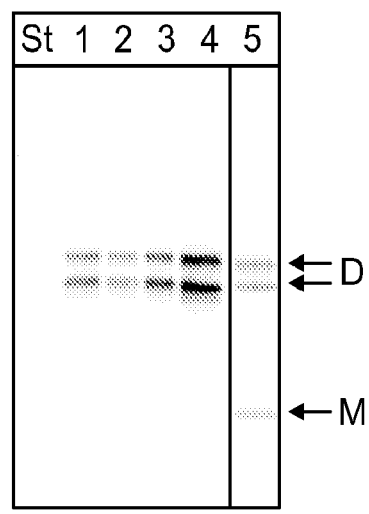
FIG. 8. Western blot of basement membranes isolated from four different human tumors shows the presence of collagen IVα1 NC1 domain dimers but not monomers. Lanes: 1-HEK 293 tumor; 2-A-549 tumor; 3-Wilms' tumor #1; 4-Wilms' tumor #2; 5—normal human GBM. The position of NC1 dimers (D) and monomers (M) is indicated with arrows.

Given that sulfilimine crosslinks function as molecular fasteners which stabilize collagen IV networks in BM, it was hypothesized that perturbation of their biosynthesis has an effect on tumor microvascular permeability and angiogenesis. Thus, it was tested whether the sulfilimine crosslinks are formed in BM of blood vessels of newly developed tumors and tumor-derived cell lines. BM were isolated from tumors formed by two human tumorigenic cell lines, kidney-derived HEK 293 and lung carcinoma A-549, grown subcutaneously in nude mice. BM were isolated from two individual specimens of primary Wilms' tumor (nephroblastoma), which typically occurs in children's kidney, and glomerular basement membrane (GBM) from normal human kidneys. Western blot analysis of these samples using monoclonal antibodies specific for α1 NC1 domain of collagen IV demonstrate that tumor BM, which are predominantly originated from microvasculature, are exclusively composed of NC1 domain dimers (FIG. 8, lanes 1-4) while normal kidney GBM is composed of both NC1 dimers and monomers (FIG. 8, lane 5). NC1 dimers are the result of covalent crosslinking of NC1 domain by sulfilimine linkage. Thus, these findings suggest that tumor cells are actively synthesizing sulfilimine crosslinks for the assembly of new blood vessel BM, a process that is crucial for development and growth of tumors.

Figure 10:
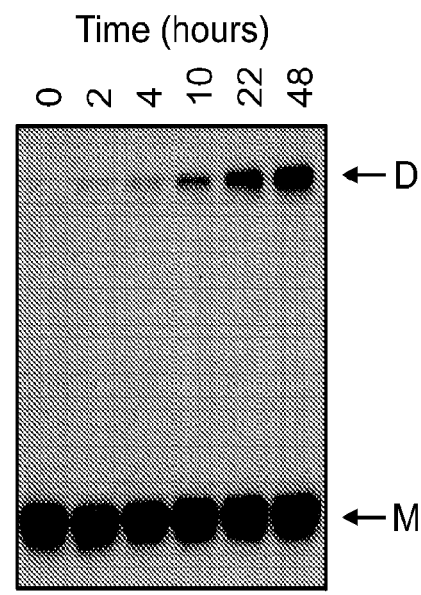
FIG. 10. Dimer formation occurs in cell free matrix preparation. Detergent insoluble PFHR9 fraction is incubated in the absence of peroxidase inhibitor and demonstrates partial recovery of dimer formationn in vitro. D=NC1 dimer; M=NC1 monomer.
Figure 11:
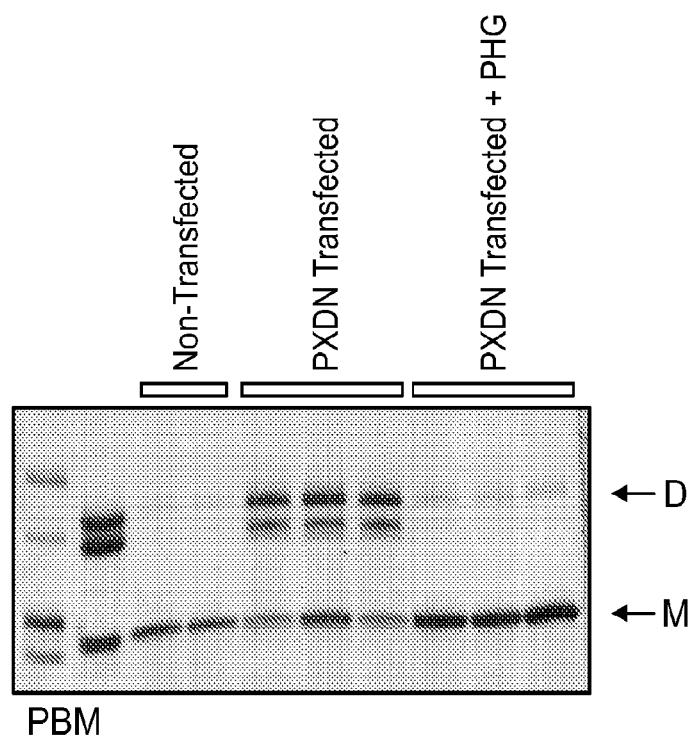
FIG. 11. PXDN mediates NC1 domain dimerization. HEK293 stably transfected with human peroxidasin (PXDN) plated on top of monomeric PFHR9 matrix leads to NC1 domain dimerization (middle lanes). In contrast, non-transfected HEK293 cells (left lanes) or PXDN transfected HEK293 cells in the presence of the peroxidase inhibitor phloroglucinol (PHG; right lanes) fail to lead to dimerization. Placental basement membrane (PBM) NC1 domain is shown for comparison.

The inventors extend this work to demonstrate that this peroxidase activity lies within the extracellular matrix expressed in culture by the HR-9 cells (FIG. 10). Based on these findings, they pursued peroxidasin, a known matrix peroxidase, as a possible candidate for collagen IV dimer and presumably sulfilimine bond formation. To demonstrate this, the inventors developed HEK293 cells stably transfected with human peroxidasin and seeded these cells on top of a monomeric NC1 (uncrosslinked) matrix and found that this selectively led to NC1 dimer formation. No dimer formation was observed with untransfected HEK293 cells or when the peroxidase inhibitor phloroglucinol was included (FIG. 11). Peroxidasin was also identified as an endogenous component of the extracellular matrix produced by the HR-9 cells with the use of mass spectrometry. Overall, the results indicate that peroxidasin is the enzyme that catalyzes the formation of the sulfilimine bond.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aouacheria et al., *Mol. Biol. Evol.*, 23:2288, 2006.
Borza et al., *J. Biol. Chem.*, 280:27147, 2005.
Cheng et al., *Free Radic. Biol. Med.*, 45:1682, 2008.
Cope et al., *J. American Chemical Soc.*, 82:4663, 1960.
Cortez et al., *Arch. Biochem. Biophys.*, 254(2):504-8, 1987.
Fox et al., *Cell*, 129:179, 2007.
Gilchrist and Moody, *Chemical Rev.*, 77:409, 1977.
Glass and Duchek, *J. American Chemical Soc.*, 98:965, 1976.
Gould et al., *N. Engl. J. Med.*, 354:1489, 2006.
Gould et al., *Science*, 308:1167, 2005.
Hudson et al., *N. Engl. J. Med.*, 348:2543, 2003.
Hynes, *Cell*, 110:673, 2002.
Kay et al., *J. American Chemical Soc.*, 114:10663, 1992.
Khoshnoodi et al., *J. Biol. Chem.*, 281:6058, 2006.
Khoshnoodi et al., *Microsc. Res. Tech.*, 71:357, 2008.
Kivirikko and Pihlajaniemi, *Adv. Enzymol. Relat. Areas Mol. Biol.*, 72:325, 1998.
Lagerwerf et al., *Rapid Commun. Mass Spectrom.*, 10:1905, 1996.
Lambeth and Swank, *Federation Proc.*, 38:830, 1979.
Licklider et al., *Anal. Chem.*, 74:3076, 2002.
Moser et al., *Science*, 324:895, 2009.
Nelson et al., *Embo J.*, 13:3438, 1994.
Palmer et al., *J. Magnetic Resonance*, 93:151, 1991.
Reid et al., *J. Proteome Res.*, 3:751, 2004.
Schleucher et al., *J. Biomol. NMR*, 4:301, 1994.
Siebold et al., *Eur. J. Biochem.*, 176:617, 1988.
Strejan et al., *Prog Clin Biol Res.*, 146:429-34, 1984.
Sundaramoorthy et al., *J. Biol. Chem.*, 277:31142, 2002.
Than et al., *Biological Chemistry*, 386:759, 2005.
Than et al., *Proc. Natl. Acad. Sci. USA*, 99:6607, 2002.
Thorner et al., *J. Biol. Chem.*, 271:13821, 1996.
Vanacore et al., *J. Biol. Chem.*, 279:44723, 2004.
Vanacore et al., *J. Biol. Chem.*, 280:29300, 2005.
Vanacore et al., *J. Biol. Chem.*, 283:22737, 2008.
Weber et al., *Eur. J. Biochem.*, 139:401, 1984.
Willker et al., *Magnetic Resonance in Chemistry*, 31:287, 1993.
Yates et al., *Anal. Chem.*, 67:1426, 1995.
Yurchenco and Furthmayr, *Biochemistry*, 23:1839, 1984.

The invention claimed is:

1. A method of creating or strengthening a sulfilimine crosslink in a subject in need of collagen IV networks, comprising administering to the subject an effective amount of an inhibitor of peroxidasin function or expression.

2. The method of claim 1, wherein the sulfilimine crosslink is between two or more peptides.

3. The method of claim 1, wherein the sulfilimine crosslink is within a peptide.

4. The method of claim 2, wherein the peptide is collagen IV.

5. The method of claim 4, wherein the agent is a nucleic acid, a protein, or a small molecule.

6. The method of claim 5, wherein the antibody a monoclonal antibody that binds immunologically to human peroxidasin, the peptide is a fragment of human peroxidasin or a human peroxidasin substrate, or the nucleic acid is an siRNA or miRNA that inhibits synthesis of human peroxidasin.

* * * * *